United States Patent
Vergyri et al.

(10) Patent No.: US 10,726,846 B2
(45) Date of Patent: Jul. 28, 2020

(54) VIRTUAL HEALTH ASSISTANT FOR PROMOTION OF WELL-BEING AND INDEPENDENT LIVING

(71) Applicant: SRI International, Menlo Park, CA (US)

(72) Inventors: Dimitra Vergyri, Sunnyvale, CA (US); Diego Castan Lavilla, Mountain View, CA (US); Girish Acharya, Redwood City, CA (US); David Sahner, Santa Cruz, CA (US); Elizabeth Shriberg, Berkeley, CA (US); Joseph B Rogers, Belmont, CA (US); Bruce H Knoth, San Carlos, CA (US)

(73) Assignee: SRI INTERNATIONAL, Menlo Park, CA (US)

( * ) Notice: Subject to any disclaimer, the term of this patent is extended or adjusted under 35 U.S.C. 154(b) by 40 days.

(21) Appl. No.: 16/088,737

(22) PCT Filed: Jun. 3, 2017

(86) PCT No.: PCT/US2017/035859
§ 371 (c)(1),
(2) Date: Sep. 26, 2018

(87) PCT Pub. No.: WO2017/210661
PCT Pub. Date: Dec. 7, 2017

(65) Prior Publication Data
US 2019/0108841 A1  Apr. 11, 2019

Related U.S. Application Data

(60) Provisional application No. 62/345,610, filed on Jun. 3, 2016.

(51) Int. Cl.
*G10L 17/00* (2013.01)
*A61B 5/00* (2006.01)
(Continued)

(52) U.S. Cl.
CPC ............ *G10L 17/005* (2013.01); *A61B 5/117* (2013.01); *A61B 5/48* (2013.01); *A61B 5/4803* (2013.01);
(Continued)

(58) Field of Classification Search
CPC ...... G06F 3/167; G06F 21/32; G06F 19/3418; H04N 21/42203; G10L 2021/02166;
(Continued)

(56) References Cited

U.S. PATENT DOCUMENTS 6,231,500 B1 * 5/2001 Kehoe .................... A61F 5/58
600/23
6,416,471 B1 * 7/2002 Kumar ................ G06F 19/3418
600/300

(Continued)

OTHER PUBLICATIONS

Al Hemairy, M., Amin, S., Hijji, M., Serhani, M., & Al Ahmed, M. (Aug. 2016). Integrated and Scalable Architecture for Providing Cost-Effective Remote Health Monitoring. In 2016 9th International Conference on Developments in eSystems Engineering (DeSE) (pp. 74-80). IEEE.*

(Continued)

*Primary Examiner* — Edgar X Guerra-Erazo
(74) *Attorney, Agent, or Firm* — Hickman Palermo Becker Bingham LLP; Christine E. Orich

(57) ABSTRACT

An electronic device for providing health information or assistance includes an input configured to receive at least one type of signal selected from sound signals, verbal signals, non-verbal signals, and combinations thereof, a communication module configured to send information related to the at least one user and his/her environment to a remote device, including the sound signals, non-verbal signals, and verbal signals, the remote device being configured to analyze a condition of the at least one user and communicate condition signals to the electronic device, a process- (Continued)

ing module configured to receive the condition signals and to cause the electronic device to engage in a passive monitoring mode or an active engagement and monitoring mode, the active engagement and monitoring mode including, but not limited to, verbal communication with the at least one user, and an output configured to engage the at least one user in verbal communication.

20 Claims, 12 Drawing Sheets

(51) Int. Cl.
    *A61B 5/117* (2016.01)
    *G10L 17/06* (2013.01)
    *G10L 25/78* (2013.01)

(52) U.S. Cl.
    CPC .......... *A61B 5/7267* (2013.01); *A61B 5/7282* (2013.01); *A61B 5/749* (2013.01); *G10L 17/06* (2013.01); *G10L 25/78* (2013.01); *A61B 2503/08* (2013.01); *A61B 2560/0247* (2013.01)

(58) Field of Classification Search
    CPC ....... G10L 15/00; G10L 17/005; G10L 17/26; G10L 25/00; G10L 25/48; G10L 25/63; A61B 5/0022; A61B 5/16; A61B 5/4803; A61B 5/749; A61B 5/7264; G16H 10/60
    See application file for complete search history.

(56) References Cited

U.S. PATENT DOCUMENTS

| | | | | |
|---|---|---|---|---|
| 8,821,415 | B2* | 9/2014 | Al-Ali | A61B 7/003 600/586 |
| 8,905,927 | B2* | 12/2014 | Cheung Hyen | A61B 5/747 600/301 |
| 2003/0101078 | A1* | 5/2003 | Voegeli | A61B 5/0002 705/2 |
| 2004/0059205 | A1* | 3/2004 | Carlson | A61B 5/0006 600/310 |
| 2007/0208558 | A1* | 9/2007 | de Matos | H04R 3/005 704/226 |
| 2008/0249376 | A1 | 10/2008 | Zaleski | |
| 2010/0286490 | A1 | 11/2010 | Koverzin | |
| 2011/0015496 | A1* | 1/2011 | Sherman | A61B 5/0006 600/301 |
| 2012/0191476 | A1 | 7/2012 | Reid et al. | |
| 2012/0265024 | A1* | 10/2012 | Shrivastav | A61B 5/40 600/300 |
| 2013/0085758 | A1 | 4/2013 | Csoma et al. | |
| 2013/0090567 | A1* | 4/2013 | Lee | A61B 7/003 600/529 |
| 2019/0272725 | A1* | 9/2019 | Viklund | A61B 5/6898 |

OTHER PUBLICATIONS

The International Bureau of WIPO, "International Preliminary Report on Patentability", in application No. PCT/US2017/035859, dated Dec. 4, 2018, 11.

Current Claims in application No. PCT/US2017/035859, dated Dec. 2018, 9 pages.

International Searching Authority, "Written Opinion" in application No. PCT/US2017/035859, dated Aug. 16, 2017, 10 pages.

International Searching Authority, "Search Report" in application No. PCT/US2017/035859, dated Aug. 16, 2017, 2 pages.

* cited by examiner

VIRTUAL HEALTH ASSISTANT FOR PROMOTION OF WELL-BEING AND INDEPENDENT LIVING

CROSS-REFERENCE TO RELATED APPLICATIONS

This application is a U.S. National Stage Patent Application filed under 35 U.S.C. § 371 of International Patent Application No. PCT/US17/35859 filed Jun. 3, 2017, which claims priority to U.S. Provisional Application Ser. No. 62/345,610, filed Jun. 3, 2016, the entire contents of all of which are hereby incorporated by reference as if fully set forth herein for all purposes.

STATEMENT REGARDING FEDERALLY SPONSORED RESEARCH

N/A

BACKGROUND

The present disclosure relates, generally, to systems and methods for providing a virtual health assistant. More particularly, the present disclosure relates to improved systems and methods for providing a virtual health assistant that can adaptively monitor a person, for example, a patient being monitored for medical reasons.

One exemplary target population who may benefit from the disclosed system and methods is the elderly population (i.e., individuals aged 65 and over). The population aged 65 and over is the fastest growing in the US. It is expected to enlarge from 50 million in 2016 to 56 million by 2020 and 73 million by 2030. More than a million new caregivers are required to support this population in the next eight years. Although home-based primary elderly care has shown promise as a cost saving measure in pilot programs, caregivers need technological solutions that would enable them to prioritize visits in order to enhance efficiency and free up bandwidth to do more.

SUMMARY

Disclosed are example systems and methods that can serve as virtual caregiver assistants and physician extenders that help ensure the health and security of persons (such as seniors and the infirm) who may spend a significant amount of time in their homes (or other settings, such as healthcare facilities). The sounds of a person and the sounds in a person's environment can be monitored in real-time, as part of "passive" monitoring, to detect anomalous or unexpected sound signals that could indicate threatening circumstances or high-risk situations. If such an sound signal is detected, "active" monitoring may engage to implement automated solutions in a closed loop fashion through, for example, structured bidirectional interactions with the person, assessment of pathologic speech/response patterns, analysis of data about the person and his/her environment (current and historical), etc., to facilitate timely medical evaluations for acute and chronic conditions, and otherwise to better monitor and enhance the person's well-being. By capturing and analyzing sounds, a user can be monitored continuously and in a greater number of situations (even while, for example, the user is in a lavatory where he or she may not want a person to follow, or a camera to be installed). The disclosed systems and methods can assist health professionals and family members take care of persons in their homes or elsewhere by better monitoring their environment while respecting their privacy.

In an illustrative embodiment a system for providing health information or assistance includes at least one electronic device configured to engage in verbal communication with at least one user based upon at least one type of signal selected from the group consisting of 1) sound signals from the at least one user's environment, 2) non-verbal signals from the at least one user, 3) verbal signals from the user; and 4) any combination of (1), (2), and (3). The electronic device may include an input configured to receive the sound signals from the at least one user's environment, the non-verbal signals from the at least one user, and the verbal signals for the at least one user and a communication module configured to send information related to the at least one user and the at least one user's environment, including the sound signals, the non-verbal signals, and the verbal signals, to a remote device, and to subsequently receive condition signals from the remote device. The electronic device may further include a processing module configured to receive the condition signals and to cause the electronic device to operate in a passive monitoring mode or an active engagement and monitoring mode, the active engagement and monitoring mode including, but not limited to, verbal communication with the at least one user and an output configured to engage the at least one user in specific types of verbal communication selected from a group consisting of: 1) asking the at least one user a question; 2) providing related suggestions to the user; and 3) provide information to the user. The system may further include a remote that may include a remote communication module configured to receive the information related to the sound signals, the non-verbal signals, and the verbal signals from the at least one electronic device, and to subsequently send the condition signals to the at least one electronic device and a rules module configured to determine, based on the sound signals, the non-verbal signals, and the verbal signals, a responsive action, wherein the responsive action is communicated from the remote device to the at least one electronic device in the form of condition signals In some embodiments, at least one of the electronic device and the remote device further includes a speaker identification module configured to identify and authenticate the at least one user.

In some embodiments, the remote device includes a temporal database configured to receive and store the information related to the at least one user and the at least one user's environment and a decisions database configured to receive and store decisions from at least one health care provider.

In some embodiments, the remote device includes a training module configured to selectively retrieve the information related to the at least one user and the at least one user's environment from the temporal database, selectively retrieve the decisions from the at least one health care provider from the decisions database, and adapt the rules module using machine learning based on the retrieved information and decisions to increase accuracy of the responsive action.

In some embodiments, the at least one electric device includes a plurality of electronic devices, the at least one user includes a plurality of users using the plurality of electronic devices, and wherein the training module is further configured to selectively retrieve information about each of the plurality of users and each of a plurality of users' environments, selectively retrieve decisions from at least one health care provider, and adapt the rules module using machine learning based on the retrieved information and decisions to increase accuracy of the responsive action.

In some embodiments, the communication module of the at least one electronic device is configured to retrieve the information related to the at least one user, the at least one user's environment, and the decisions from the at least one health care provider, and the at least one electronic device includes a report module configured to produce a report to the at least one user regarding the information related to the at least one user, the at least one user's environment, and the decisions from the at least one health care provider.

In some embodiments, when operating in the passive monitoring mode, t a remote device processing module is configured to analyze the sound signals to extract passive user information, determine, from the passive user information, whether an active trigger event has occurred, and upon determining that the active trigger event has occurred, cause the electronic device transition to the active engagement and monitoring mode.

In some embodiments, upon transitioning to the active engagement and monitoring mode, the electronic device processing module is configured to engage the at least one user via the verbal communication through the output and the remote device processing module is configured to verify and augment the passive user information through the communication with the user.

In some embodiments, upon transitioning to the active engagement and monitoring mode, the remote device processing module is configured to analyze the sound signal from the input to extract active user information associated with a communication with the at least one user and determine, from both the passive user information and the active user information, an active engagement response.

In some embodiments, upon transitioning to the active engagement and monitoring mode, the remote device processing module is configured to determine, via the verbal communication, whether the active engagement response has been completed and upon determining that the active engagement response has been completed, cause the electronic device to transition to the passive monitoring mode.

In some embodiments, the rules module adapts the verbal communication through the output in real time based on one of the passive user information and the active user information.

In some embodiments, the adaptation of the verbal communication includes changes in questions asked or the way the questions are asked to the at least one user based on changes in a condition of the at least one user detected in one of the passive user information and the active user information.

In some embodiments, the non-verbal signals are selected from the group consisting of: pitch, speed, tone, volume of voice, intonation, inflection, or other sounds that do not include words.

In some embodiments, the step of analyzing the sound signals includes at least one of analyzing speech pattern, intonation, data about the at least one user, data about the at least one user's environment, sound signals in the at least one user's environment, sounds created by the at least one user, and does not include analyzing key words.

In some embodiments, while engaging the at least one user via the verbal communication regarding the active trigger event, the rules module adapts future engagements regarding related trigger events based on information acquired during the verbal communication regarding the active trigger event.

In some embodiments, while engaging the at least one user via the verbal communication, the processing module is configured to analyze both verbal signals and non-verbal signals.

In some embodiments, each of the plurality of electronic devices is configured to produce a report and, subsequent to the training module adapting the rules module, the at least one health care provider makes a decision based on the report.

In some embodiments, the machine learning performed by the training module uses a model based on information retrieved from the temporal database and decisions retrieved from the decisions database, and the model is subsequently trained based on input from the at least one health care provider.

In some embodiments, the model is based on information from the multiple users, thereby providing a larger data set.

In some embodiments, each of the plurality of electronic devices is configured to produce a report and each of the plurality of users inputs information into a corresponding one of the plurality of electronic devices and receives output information from the corresponding one of the plurality of electronic devices.

In some embodiments, an alert is sent to a caretaker or health care professional that a responsive action was sent to the at least one user.

In another illustrative embodiment, an electronic device is provided for providing health information or assistance, wherein the electronic device is configured to engage in verbal communication with a user. The electronic device includes an input configured to receive at least one type of signal selected from the group consisting of: (1) sound signals from at least one user's environment, (2) non-verbal signals for the at least one user, 3) verbal signals from the user, and 4) any combination of (1), (2), and (3). The electronic device may further include a communication module configured to send information related to the at least one user and the at least one user's environment to a remote device, including the sound signals, non-verbal signals, and verbal signals, the remote device being configured to analyze a condition of the at least one user and subsequently communicate condition signals to the electronic device. The electronic may still further include a processing module configured to receive the condition signals and to cause the electronic device to engage in a passive monitoring mode or an active engagement and monitoring mode, the active engagement and monitoring mode including, but not limited to, verbal communication with the at least one user and an output configured to engage the at least one user in specific types of verbal communication selected from a group consisting of: 1) asking the at least one user a question; 2) providing related suggestions to the user; and 3) provide information to the at least one user.

In some embodiments, the electronic device includes a plurality of electronic devices, the at least one user includes a plurality of users using the plurality of electronic devices, and wherein the communication module of each electronic devices is configured to send information related to a respective user and the user's environment to the remote device to analyze a condition of the respective user.

In some embodiments, the communication module of the electronic device is further configured to retrieve the information related to the at least one user, the at least one user's environment, and decisions from at least one health care provider, and the at least one electronic device includes a report module configured to produce a report to the at least one user regarding the information related to the at least one user, the at least one user's environment, and the decisions from the at least one health care provider.

In some embodiments, the processing module is further configured to, upon transitioning to the active engagement and monitoring mode, engage the at least one user via communication through the output and the remote device processing module is configured to analyze the sound signal from the input to extract active user information associated with a communication with the at least one user and determine, from both the passive user information and the active user information, an active engagement response.

In some embodiments, the non-verbal signals are selected from the group consisting of: pitch, speed, tone, volume of voice, intonation, inflection, or other sounds that do not include words.

In a further illustrative embodiment, a method of providing health information or assistance includes the steps of receiving, at an input of an electronic device, at least one type of signal selected from the group consisting of: 1) sound signals from the at least one user's environment, 2) non-verbal signals from the at least one user, 3) verbal signals from the user; and 4) any combination of (1), (2), and (3) and communicating information related to the at least one user and the at least one user's environment to a remote device, the remote device being configured to analyze a condition of the at least one user and subsequently communicate condition signals to the electronic device. The method further includes the step of receiving, at the electronic device, a condition signal from the remote device to engage in a passive monitoring mode or an active engagement and monitoring mode, the active engagement and monitoring mode including, but not limited to, verbal communication with the at least one user selected from a group consisting of: 1) asking the at least one user a question; 2) providing related suggestions to the user; and 3) provide information to the at least one user.

In some embodiments, in the passive monitoring mode, the method includes the steps of analyzing the information related to the at least one user and the at least one user's environment, extracting passive user information, determining, from the passive user information, whether a trigger event has occurred, and upon determining that the trigger event has occurred, transitioning the electronic device to the active engagement and monitoring mode.

In some embodiments, in the active engagement and monitoring mode, the method includes the steps of engaging the at least one user via verbal communication through an output of the electronic device, analyzing, at the remote device, the information related to the at least one user and the at least one user's environment to extract active user information associated with the verbal communication with the at least one user, and determining, at the remote device, from both the passive user information and the active user information, an active engagement response.

In some embodiments, the method includes the steps of determining, via verbal communication, whether the active engagement response has been completed and upon determining that the active engagement response has been completed, transitioning to the passive monitoring mode.

In some embodiments, the method includes the step of adapting the verbal communication with the at least one user in real time based on one of the passive user information and the active user information.

In some embodiments, the step of adapting the verbal communication includes the step of changing questions asked of the at least one user based on changes in a condition of the at least one user detected in one of the passive user information and the active user information.

In some embodiments, the step of analyzing the information related to the at least one user and the at least one user's environment includes analyzing, at the remote device, speech pattern, intonation, data about the at least one user, data about the at least one user's environment, sound signals in the at least one user's environment, or sounds created by the at least one user, and does not include analyzing key words.

In some embodiments, the method includes the steps of receiving and storing the information related to the at least one user and the at least one user's environment and receiving and storing decisions from at least one health care provider.

In some embodiments, the method includes the steps of retrieving information related to the at least one user and the at least one user's environment from a temporal database, retrieving the decisions from the at least one health care provider from a decisions database, and adapting rules using machine learning based on the retrieved information and decisions to increase accuracy of an action to be taken with respect to the at least one user.

In some embodiments, the at least one electronic device includes a plurality of electronic devices, the at least one user comprises a plurality of users using the plurality of electronic devices, and the method includes the steps of retrieving information about each of the plurality of users and each of a plurality of users' environments, retrieving decisions from the at least one health care provider, and adapting rules using machine learning based on the retrieved information and decisions to increase accuracy of the action to be taken.

In some embodiments, the method includes the step of producing a report regarding the information related to the at least one user, the at least one user's environment, and the decisions from the at least one health care provider.

In yet another illustrative embodiment, a non-transitory computer-readable medium tangibly comprising computer program instructions in which the instructions, when executed by a process, cause the processor to receive input in the form of at least one type of signal selected from the group consisting of: 1) sound signals from the at least one user's environment, 2) non-verbal signals from the at least one user, 3) verbal signals from the user; and 4) any combination of (1), (2), and (3). The instructions further cause the processor to send information related to the at least user and the at least one user's environment, including the sound signals, the non-verbal signals, and the verbal signals, to a remote device, the remote device being configured to analyze a condition of the at least one user and subsequently communicate condition signals to the processor and receive the condition signals at the processor. The instructions further cause the processor to cause the processor to engage in a passive monitoring mode or an active engagement and monitoring mode, the active engagement and monitoring mode including, but not limited to, verbal communication with the at least user, wherein the electronic device is configured to transition from the passive monitoring mode to the active engagement and monitoring mode when the condition signals indicate that the at least user is in need of assistance and is further configured to transition from the active engagement and monitoring mode to the passive monitoring mode when the condition signals indicate that the at least user is no longer in need of assistance.

The foregoing and other aspects and advantages of the present disclosure will appear from the following description. In the description, reference is made to the accompanying drawings that form a part hereof, and in which there is shown by way of illustration one or more exemplary versions. These versions do not necessarily represent the full scope of the invention.

BRIEF DESCRIPTION OF THE DRAWINGS

This disclosure is illustrated by way of example and not by way of limitation in the accompanying figures. The figures may, alone or in combination, illustrate one or more embodiments of the disclosure. Elements illustrated in the figures are not necessarily drawn to scale. Reference labels may be repeated among the figures to indicate corresponding or analogous elements.

The foregoing and other aspects and advantages of the invention will appear from the following description. In the description, reference is made to the accompanying drawings that form a part hereof, and in which there is shown by way of illustration preferred embodiments of the invention. Such embodiments do not necessarily represent the full scope of the invention, however, and reference is made therefore to the claims and herein for interpreting the scope of the invention.

DETAILED DESCRIPTION

Figure 1:
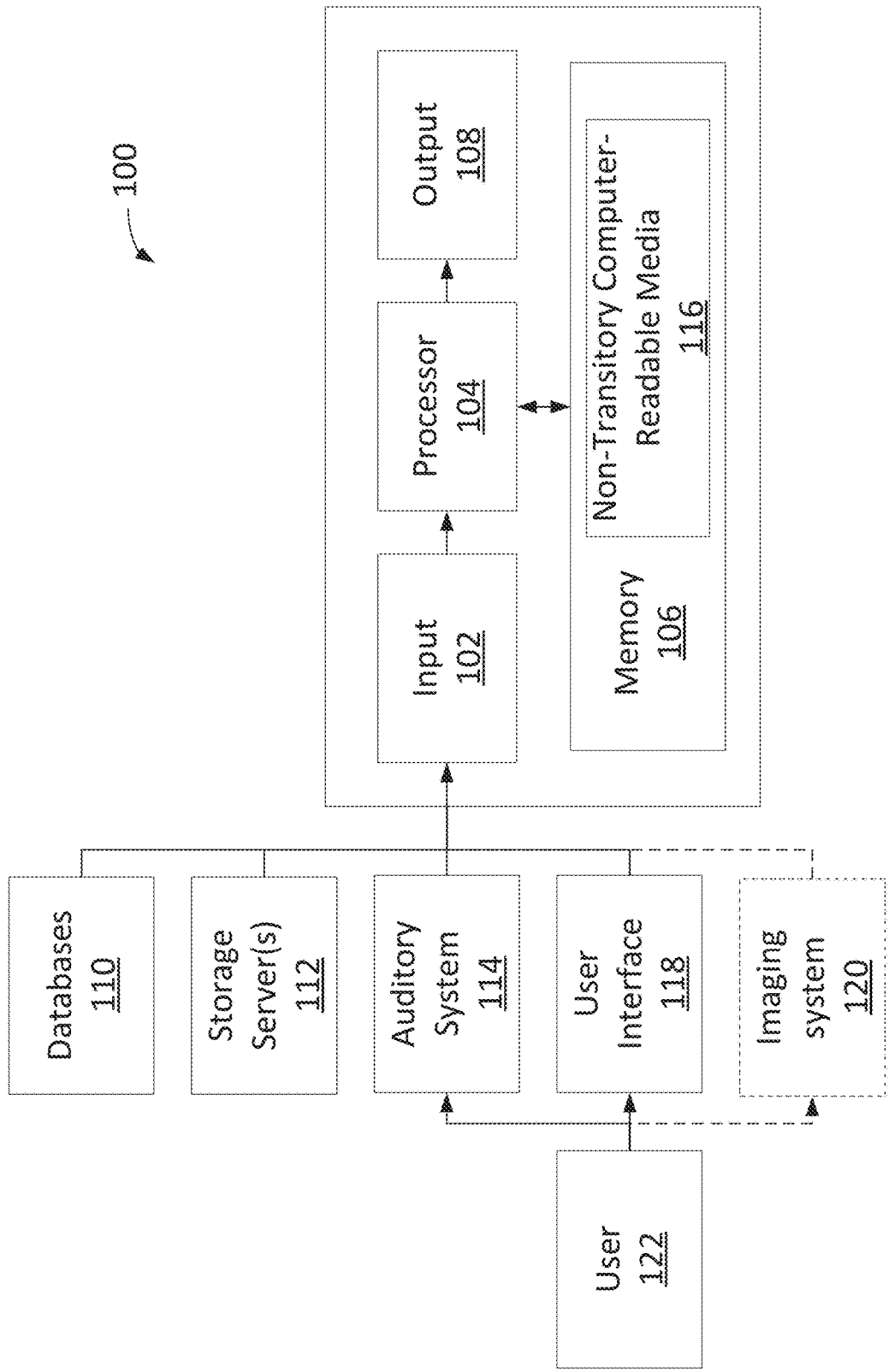
FIG. 1 depicts a simplified block diagram of an example virtual health assistant and physician extender system, in accordance with one or more embodiments of the invention.

Disclosed are example systems and methods that can use speech and sound analysis as well as virtual personal assistant capabilities to assist in monitoring and promoting the health of occupants of a home, healthcare facility, or other location. Referring to FIG. 1, a block diagram of an example system 100, in accordance with aspects of the present disclosure, is shown. As will be described in more detail below, the system 100 (or any of the systems disclosed herein) may be implemented by one or more devices, for example, local electronic or remote devices. Local electronic devices refer to user devices, for examples, devices utilized by a patient, a healthcare professional, or any other individual. Remote devices refer to devices that are remote from the local electronic devices and which may aggregate some of the processing, storage, and other functionality of multiple local electronic devices.

In general, the system 100 may include one or more inputs 102, processors 104, memories 106, and outputs 108, and may be configured to carry out steps for adaptively monitoring and analyzing sound signals created by a user or sound signals occurring in a user's environment or both, in accordance with aspects of the present disclosure. Sound signal, as used herein, refers to any sound at any frequency, including audio signals. Such sounds may include, but are not limited to, speech, snoring, coughing, sneezing, and various other sound signals, as described below.

The system 100 may include, access, or communicate with one or more databases 110, storage servers 112, auditory systems 114, user interfaces 118, and, in some implementations, an imaging system 120, by way of a wired or wireless connection to the inputs 102. In various implementations, the system 100 may include any computing device, electronic device, apparatus or system configured for carrying out instructions and providing input/output capabilities, and may operate as part of, or in collaboration with other computing devices and sensors/detectors (local and remote). In certain instances, the system 100 may be a portable or mobile device, such as a smartphone, laptop, tablet, and the like. In alternative embodiments, it may be a standalone appliance with these capabilities. In this regard, the system 100 may be a system that is designed to integrate a variety of software and hardware capabilities and functionalities, and/or may be capable of operating autonomously. In addition, in various configurations, the components illustrated in FIG. 1 may be implemented using multiple separate components, and similarly, multiple illustrated components can be combined into one component.

The input 102 may include any one or more different input elements, such as a mouse, keyboard, touchpad, touch screen, buttons, microphone, a personal tracking device (e.g., a Fitbit or other tracking device), other electronic inputs, and the like, for receiving various sound signals, selections, and operational instructions from a user through touch, movement, speech, etc. The input 102 may also include various drives and receptacles, such as flash-drives, USB drives, CD/DVD drives, and other computer-readable medium receptacles, for receiving various data and information. To this end, input 102 may also include various communication ports and modules, such as Ethernet, Bluetooth, or WiFi, for exchanging data and information with these, and other external computers, systems, devices, machines, mainframes, servers or networks.

In addition to being configured to carry out various steps for operating the system 100, the processor 104 may be configured to execute instructions, stored in the memory 106 in a non-transitory computer-readable media 116. The instructions executable by the processor 104 may correspond to various virtual health assistant (VHA) systems, examples of which will be described below. Although the non-transitory computer-readable media 116 is shown in FIG. 1 as included in the memory 106, it may be appreciated that instructions executable by the processor 104 may be additionally or alternatively stored in another data storage location having non-transitory computer-readable media.

In some aspects, the processor 104 may be configured to receive and process a sound signal and/or a picture or video signal to generate a variety of information, including patient responses, signals from personal tracking device, user events, hypothesis confidence levels, as well as other data. In some aspects, the processor 104 may access information and data, including sound signals and video signals, stored in or emitted by the imaging system 120, the user interface 118, the auditory system 114, the storage server(s) 112, the database(s) 110, or other data storage locations using the input 102. In some aspects, the auditory system 114 may acquire a sound signal continuously using, for example, a microphone or other audio or sound recording device to continuously or periodically record a user or the user's environment 122. In some aspects, the imaging system 120 may acquire either a single image or a continuous video signal using, for example, a camera, an infrared scanning system, or any other image capturing or video recording device that can be used to periodically image and/or scan and/or continuously record the user 122.

The system 100 may be comprised of only local electronic devices, one remote device and multiple local electronic devices, multiple remote devices and multiple local electronic devices, or any combination thereof.

The system 100 may include one or more local electronic devices that include any one or more of the components depicted in FIG. 1. In one illustrative embodiment, one or more local electronic devices may include an auditory system 114, a user interface 120, an input 102, a processor 104, an output 108, memory 106, and non-transitory computer-readable media 116. In other embodiments, one or more local electronic devices may include all of the components depicted in FIG. 1. In still other embodiments, one or more local electronic devices may include any number of the components depicted in FIG. 1. Each local electronic device need not include the same components. In other words, the components (depicted in FIG. 1) may vary from one local electronic device to another.

The system 100 may include one or more remote devices, which may include any one or more of the components depicted in FIG. 1. In an illustrative embodiment, one or more remote devices may include an input 102, a processor 104, memory 106, output 108, databases 110, storage server(s) 112, and non-transitory computer-readable media 116. In other embodiments, one or more remote device may include any number of components depicted in FIG. 1. Further, each remote device need not include the same components and components may vary from one remote device to another.

As should be clear, while only one of each of the components in FIG. 1 is depicted, there may be more than one of each of the components of FIG. 1 within the system 100, as the components may be duplicated between the remote device and one or more local electronic devices.

Embodiments of the present invention may be described with reference to flowchart illustrations of methods and systems according to embodiments of the technology, and/or algorithms, formulae, or other computational depictions, which may also be implemented as computer program products. In this regard, each block or step of a flowchart, and combinations of blocks (and/or steps) in a flowchart, algorithm, formula, or computational depiction can be implemented by various means, such as hardware, firmware, and/or software including one or more computer program instructions embodied in computer-readable program code logic. As will be appreciated, any such computer program instructions may be loaded onto the system 100 as described with reference to FIG. 1, as well as any other computer, including without limitation a general purpose computer or special purpose computer, or other programmable processing apparatus to produce a machine, such that the computer program instructions which execute on the computer or other programmable processing apparatus create means for implementing the functions specified in the block(s) of the flowchart(s).

Accordingly, blocks of the flowcharts, algorithms, formulae, or computational depictions support combinations of means for performing the specified functions, combinations of steps for performing the specified functions, and computer program instructions, such as instructions embodied in computer-readable program code logic means, for performing the specified functions. It will also be understood that each block of the flowchart illustrations, algorithms, formulae, or computational depictions and combinations thereof described herein, can be implemented by special purpose hardware-based computer systems which perform the specified functions or steps, or combinations of special purpose hardware and computer-readable program code logic means.

Furthermore, these computer program instructions, such as instructions embodied in computer-readable program code logic, may also be stored in a computer-readable memory in the form of non-transitory computer-readable media, that can direct a computer or other programmable processing apparatus to function in a particular manner, such that the instructions stored in the computer-readable memory produce an article of manufacture including instruction means which implement the function specified in the block(s) of the flowchart(s). The computer program instructions may also be loaded onto a computer or other programmable processing apparatus to cause a series of operational steps to be performed on the computer or other programmable processing apparatus to produce a computer-implemented process such that the instructions which execute on the computer or other programmable processing apparatus provide steps for implementing the functions specified in the block(s) of the flowchart(s), algorithm(s), formula(e), or computational depiction(s).

It will further be appreciated that the terms "programming" or "program executable" as used herein refer to one or more instructions that can be executed by a processor to perform a function as described herein. The instructions can be embodied in software, in firmware, or in a combination of software and firmware. The instructions can be stored local to the device in non-transitory media, or can be stored remotely such as on a server, or all or a portion of the instructions can be stored locally and remotely. Instructions stored remotely can be downloaded (pushed) to the device by user initiation, or automatically based on one or more factors. It will further be appreciated that as used herein, that the terms processor, computer processor, central processing unit ("CPU"), and computer are used synonymously to denote a device capable of executing the instructions and communicating with input/output interfaces and/or peripheral devices.

Figure 2:
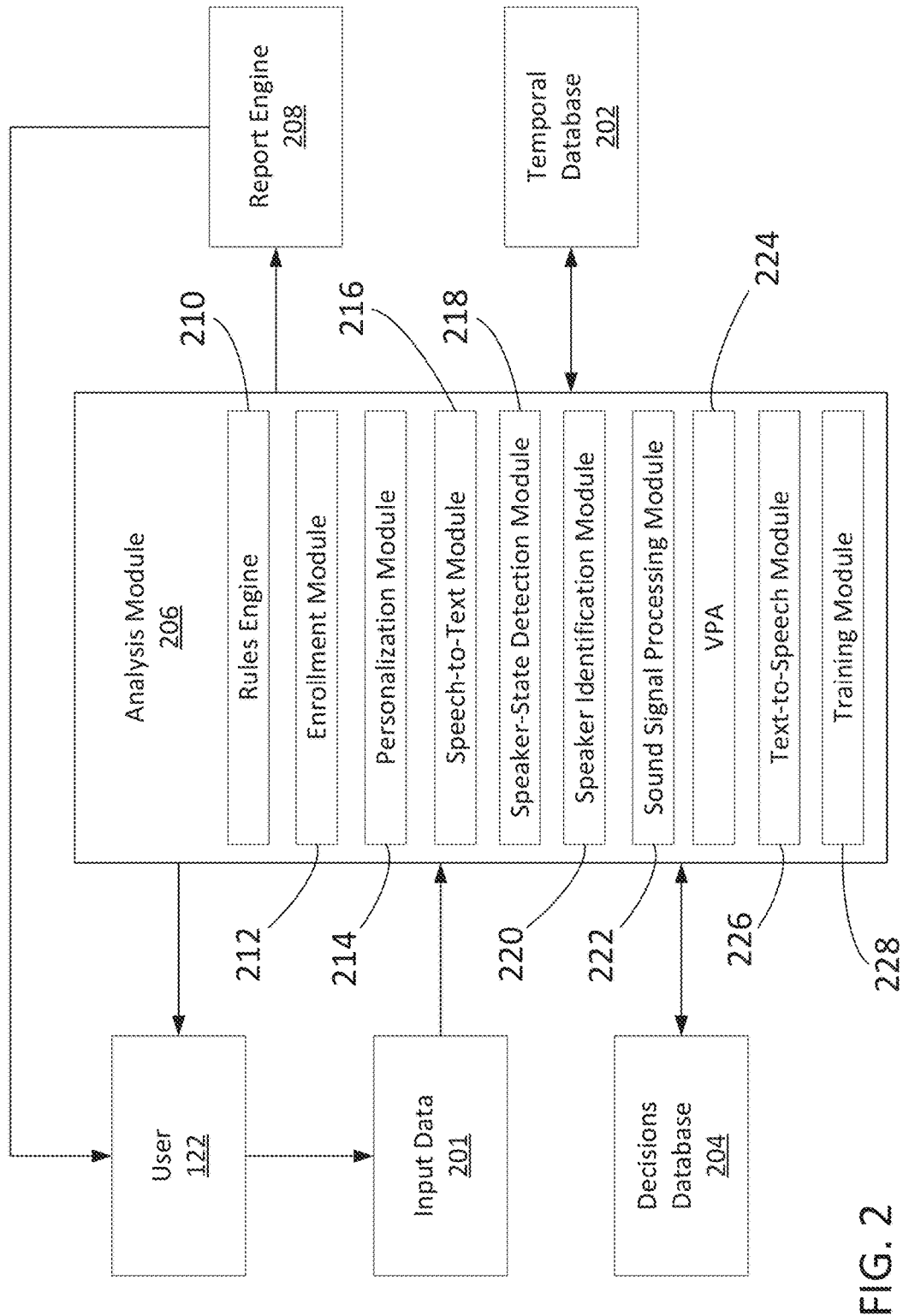
FIG. 2 depicts a simplified block diagram of an example virtual health assistant system and hardware and software components thereof, in accordance with one or more embodiments of the invention.
Figure 9:
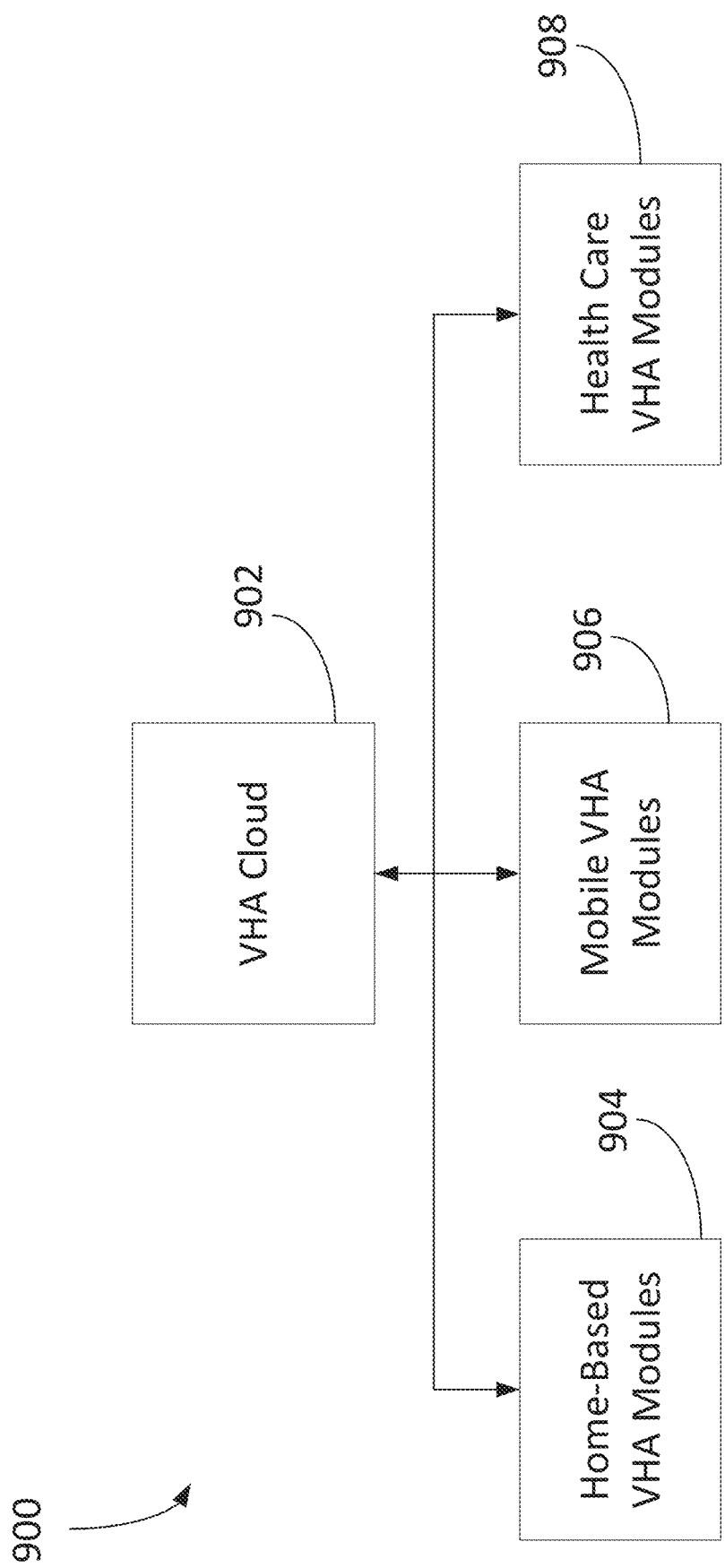
FIG. 9 is simplified block diagram of an example virtual health assistant and physician extender system, in accordance with one or more embodiments of the invention.

Referring now to FIG. 2, a block diagram of an example VHA system 200 is shown, wherein steps performed within the VHA system 200 may be executed by the processor 104. For example, the processor 104 may receive input data 201 from the user 122 through the input 102 (which can then be monitored and analyzed using the illustrated VHA system 200), as described in detail below. As best seen in FIG. 9, the user 122 can be a patient, a healthcare professional, a medical technician, or any other person interacting with the VHA module 200.

It should be noted that any of the components (202, 204, 206, 208 (including 210, 212, 214, 216, 218, 220, 222, 224, 226, and 228)) may be implemented by one or more local electronic devices and/or one or more remote devices, as will be discussed in greater detail below.

It should be noted that the following description of the VHA system 200, as well as the accompanying figures, are meant to be illustrative and are in no way meant to be limiting. Other VHA systems can be arranged differently and can include different components or modules, while still being capable of performing the features disclosed in the present application.

As illustrated, the VHA system 200 can include a temporal database 202, a decisions database 204, an analysis module 206, and/or a report engine 208. In some embodiments, the temporal database 202, the decisions database 204, the analysis module 206, and/or the report engine 208 may be implemented on a local electronic device that a user may use in his or her home or care facility or a healthcare professional may use in his or her office. In other embodiments, one or more of the temporal database 202, the decisions database 204, the analysis module 206, and/or the report engine 208 may be implemented on a remote device, for example, on one or more devices associated with a VHA cloud 902, as seen in FIG. 9 that interact with a local device having a VHA module. In still other embodiments, both the electronic device and the remote device may include one or more of the temporal database 202, the decisions database 204, the analysis module 206, and/or the report engine 208. In an illustrative embodiment, the temporal database 202, the decisions database 204, the analysis module 206, and the report engine 208 are implemented on a remote device and the electronic devices communicate to send information and decisions back and forth, as described in more detail below.

Similar to FIG. 1, the VHA system 200 of FIG. 2 may be comprised of only local electronic devices, one remote device and multiple local electronic devices, multiple remote devices and multiple local electronic devices, or any combination of local electronic and remote devices.

The VHA system 200 may include one or more local electronic devices, which may include any one or more of the components depicted in FIG. 2. In an illustrative embodiment, one or more local electronic devices may include the temporal database 202, the decisions database 204, the analysis module 206 or one or more sub-components of the analysis module 206, and the report engine 208. In another embodiment, one or more local electronic devices may not include any of the components (elements 202, 204, 206, and 208) of FIG. 2. In still another embodiment, one or more local electronic devices may include only the report engine 208. In still other embodiments, one or more electronic devices may include any number of components depicted in FIG. 2. Each local electronic device need not include the same components. In other words, the components (depicted in FIG. 2) may vary from one local electronic device to another.

The VHA system 200 may also include one or more remote devices, which may include any one or more of the components depicted in FIG. 2. In an illustrative embodiment, one or more remote devices may include the temporal database 202, the decisions database 204, the analysis module 206 or one or more sub-components of the analysis module 206, and the report engine 208. In another illustrative embodiment, one or more remote devices may include the temporal database 202, the decisions database 204, and the analysis module 206 or one or more sub-components of the analysis module 206. In still other embodiments, one or more remote devices may include any number of the components depicted in FIG. 2. Further, each remote device need not include the same components and components may vary from one remote device to another. s As should be clear, while only one of each of the components in FIG. 2 is depicted, there may be more than one of each of the components of FIG. 2 within the system 200, as the components may be duplicated between the remote device and one or more local electronic devices (including the sub-components of the analysis module 206).

Turning again to FIG. 2, the temporal database 202 may store medical information or any other relevant information about the patient or user 122, including all of the incoming sound signals, decisions, and actions taken by the user 122, as well as prior medical history, family medical history, demographic information, including, for example, illnesses, conditions, limitations in motion or diet, etc. The decisions database 204 stores treatment and interaction decisions made by healthcare professionals, based on sound signals, decisions, and actions taken by the user 122, as well as prior medical history of the user 122.

The analysis module 206 may receive the input data 201, which may include a user selection from a predetermined list of options, a text input, an audio or sound signal, and/or a video signal, from the input 102. As will be further described below, the analysis module 206 may additionally receive patient information stored in the temporal database 202, as well as corresponding decisions stored the decisions database 204.

The analysis module 206 comprises a rules engine 210, an enrollment module 212, a personalization module 214, a speech-to-text module 216, a speaker-state detection module 218, a speaker identification module 220, an acoustic signal processing module 222, a virtual personal assistant (VPA) 224, a text-to-speech module 226, and/or a training module 228.

The analysis module 206, along with the rest of the VHA system 200, is governed by the rules engine 210. The rules engine 210 contains a plurality of rules that collectively define the system behavior. Rules are typically in the form of predicate tests (e.g., "If Condition then Action(s)") where the condition can be tested using an explicit test (e.g., "Temperature>101") or a fuzzy test (e.g., "Breathing fast"). Rules can be predefined based on standard practice, and new rules can be added by a health care professional or other user if the existing rules do not support a required test. If a condition is met, then the rules engine can trigger one or more actions. In some instances, the actions can be queries to the user (e.g., "You seem to be coughing a lot. Should I notify your Doctor?"). The rules engine 210 continually monitors the data in the temporal database 202 and, when a specific condition is met, takes the corresponding actions.

The system behavior defined by the rules engine 210 can include: (i) The types of sound signals the VHA system 200 is passively monitoring at any given time. (ii) How passively detected sound signals may trigger active engagement. For example, detecting coughing 5 times in a period of 30 minutes may trigger a dialogue to obtain more information about the cough. (iii) How and when to engage with the user 122 for pre-scheduled interactions. For example, 3 times a week the user 122 may engage in a dialogue relevant to his ability to perform their activities of daily living. (iv) How information collected via active engagement impacts follow-up monitoring. For example, after detecting fatigue and engaging in a fatigue related dialogue, the system switches to monitoring for sound signals indicating lack of sleep, snoring, extended physical activity, etc.

As such, the rules engine 210 controls the functionality of the VHA system 200. Rules defining the behavior can be specified manually, via the user interface 118, based on common practices from nurse caregivers, health care professionals, or other persons or customized care required for the user 122 specifically. As indicated above, the VHA system 200 may adapt/adjust the rules in a pre-defined manner based on information collected previously by the VHA system 200. The user interface 118 for defining the rules may include a graphical interface enabling activation of certain rules among multiple pre-defined choices or a natural language interface (verbal and/or text).

As will be described in detail below, the rules engine 210 can be adapted and updated using manual adjustments made by the user 122 or through autonomous adjustments made by the training module 228 based on machine learning ("ML").

Upon initialization of the VHA system 200, the user 122 can initialize a profile using the enrollment module 212 and configure the VHA system 200 to preferences of the user 122 using the personalization module.

Using the enrollment module 212, the user 122 can register with the VHA system 200 and the user 122 or a caregiver, health care profession, or other person can define the type of sound signals that require monitoring for the user 122. The enrollment module 212 generally receives an auditory sample from the user 122 that, in one embodiment, can then be subsequently used with the speaker identification module 220 to identify the target user 122 among multiple people present in the same environment.

Additionally, if the VHA system 200 is equipped with the imaging system 120, the enrollment module 212 can also be used to register the user 122 using other biometric signatures, such as an infrared signature, or, if video monitoring is an acceptable option, a facial image.

In some instances, if the user 122 has not originally enrolled for a specific type of identification (e.g., voice recognition, facial recognition, etc.), and the rules engine 210 is set or updated to require that type of identification, then the user 122 could be asked to enroll or reenroll for that type of identification.

In some instances, the input data 201 is in the form of a continuous sound signal, which can contain both utterances (such as spoken words, grunts, sighs, etc.) by the user 122 and ambient sound conditions or ambient sound signals. The sound signal can be continuously analyzed using the speech-to-text module 216, the speaker-state detection module 218, the speaker identification module 220, and the sound signal processing module 222. The speech-to-text module 216 converts any utterances spoken by the user 122, contained within the sound signal, into corresponding text data. The speaker-state detection module 218 analyzes the sound associated with any utterances spoken by the user 122 to determine a state of the user 122. For example, the state of the user 122 can be one or more of fatigued, happy, bored, sad, angry, or any other state configured to be monitored by the VHA system 200. The speaker identification module 220 analyzes the sound signals associated with any utterances spoken by the user 122 to identify the user 122 with an associated probability. The sound signal processing module 222 analyzes sound signals to identify possible causes. For example, the sound signal processing module 222 may identify a cough, a cough epoch (e.g., a number of coughs in one or more time periods), a yawn, a fall, a door knock, audible wheezing, hoarseness, aphasia, dysarthria, stridor, repetitive statements, depression, delirium, mania or any other sound signals configured to be monitored by the VHA system 200.

After the input data 201 has been analyzed, the VPA 224 can be used to manage the interaction between the analysis module 206 and the user 122. This management may comprise the VPA 224 applying the text data, the state of the user 122, the identity of the user 122, the observed sound signals, and/or any other input data 201 received by the analysis module 206, as well as information retrieved from the decisions database 204 and the temporal database 202, to the rules engine 210 to determine an appropriate user interaction or dialogue, which can be in the form of text data.

Once the VPA 224 determines an appropriate response, the VPA 224 can then apply the text data to the text-to-speech module 226. The text-to-speech module 226 converts the text data to speech, which is outputted through the output 108 to the user 122. The output 108 can comprise a speaker or other audio or sound emitting device.

Periodically, or as a result of a user command, the analysis module 206 can instruct the report engine 208 to generate a report, as will be discussed in detail below.

Now that the general layout of the VHA system 200 has been described above, an example mode of operation will be described. It will be understood that the following description is in no way intended to be limiting.

Figure 3:
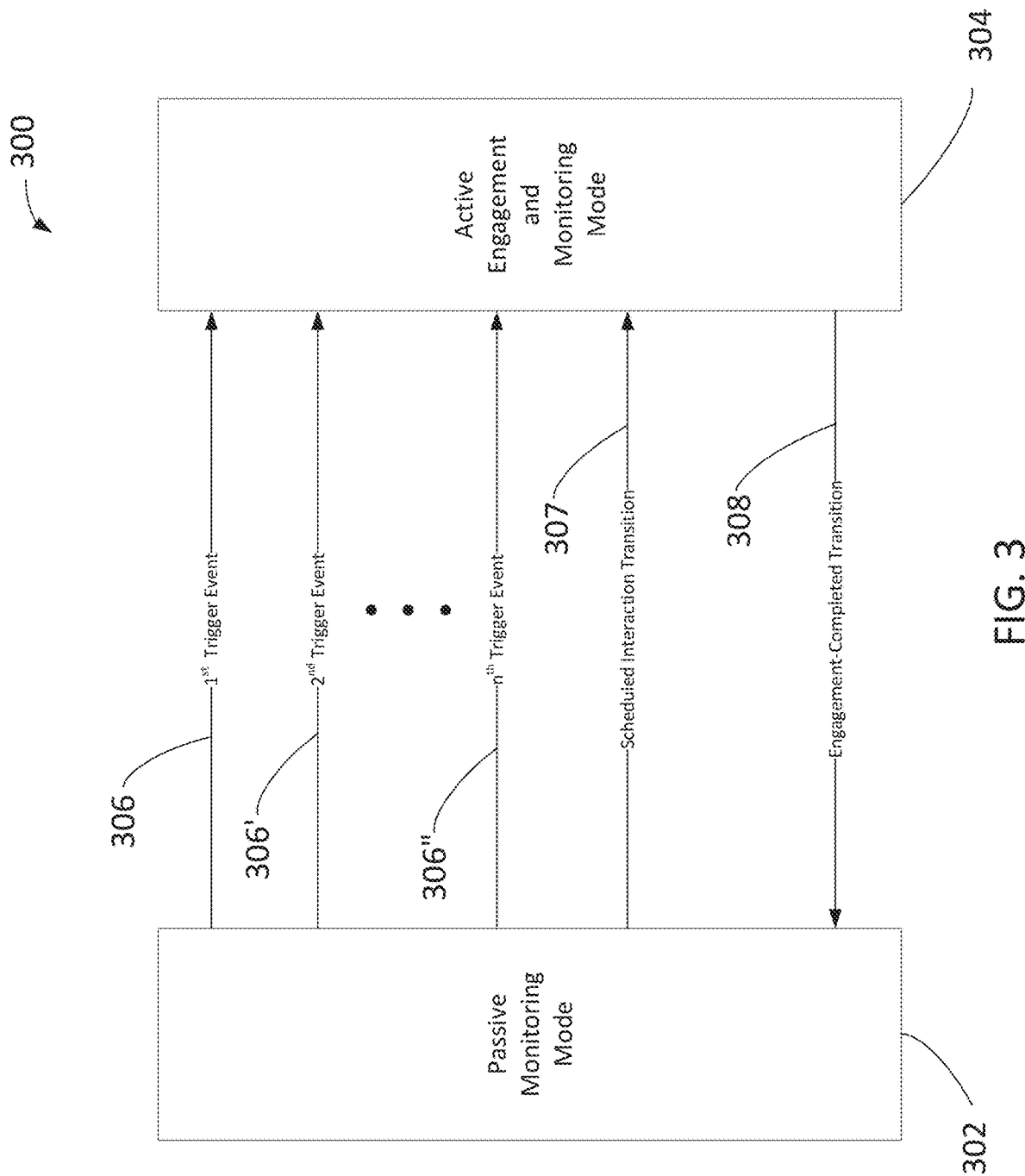
FIG. 3 is a state diagram setting forth example modes of operation for a virtual health assistant system, in accordance with one or more embodiments of the invention.

Referring now to FIG. 3, a state diagram 300 is illustrated, showing an example method of operation of the VHA system 200. As illustrated, the VHA system 200 can be operated in a passive monitoring mode 302 and an active engagement and monitoring mode 304. In the passive monitoring mode 302, the VHA system 200 monitors for sound signals in an environment of the user 122 or sound signals from the user 122 himself, but does not directly interact with the user 122. As such, passive monitoring mode 302 may be used to detect various sound signals and make inferences based on these various sound signals detected. Sound signals could include sounds made or caused by the user or by others or sounds occurring in the background, such as objects falling.

In some instances, the operation may switch from passive monitoring mode 302 to active engagement and monitoring mode 304 as a result of various trigger events 306, 306', 306" based on observed sound signals and interactions with the user 122 who is being monitored. For example, in some instances, a trigger event may pertain to various loud noises detected by the VHA system 200, in order to switch into active engagement and monitoring mode 304 to verify whether or not the user 122 needs help. In some other instances, a trigger event may pertain to an unknown speaker being detected if the VHA system 200 detects speech, but does not recognize the speaker. In some instances, the unknown speaker trigger event may be selectively turned on or off to avoid over firing in case of, for example, a party. The trigger events can be sound signal cues that do not correspond with the words spoken by user (e.g., as part of a direct communication by the user to the system), although they may correspond with how words are spoken by the user (e.g., if the user is speaking particularly slowly, repeating or slurring words, sounding as though he or she is in pain, etc.). It should be appreciated that these examples, while illustrative of the capabilities and operation of the VHA system 200, are not meant to be limiting, as any other suitable sound signals can be selectively monitored.

Additionally, the operation may switch from passive monitoring mode 302 to active engagement and monitoring mode 304 as a result of a scheduled interaction transition 307. Once the operation switches into active engagement and monitoring mode 304, the VHA system 200 may begin an active engagement or dialogue with the user 122. During the active engagement and monitoring mode 304, the VHA system 200 continues to collect data such as sound signals from the user and from the user's environment. In addition, the VHA system 200 collects data from the user 122, thereby verifying and augmenting the passive patient information through communication with the patient to increase confidence on the produced reports. Once the VHA system 200 has finished interacting or engaging with the user 122, an engagement-completed transition 308 will occur, returning the VHA system 200 to the passive monitoring mode 302 once the engagement is completed.

Figure 4:
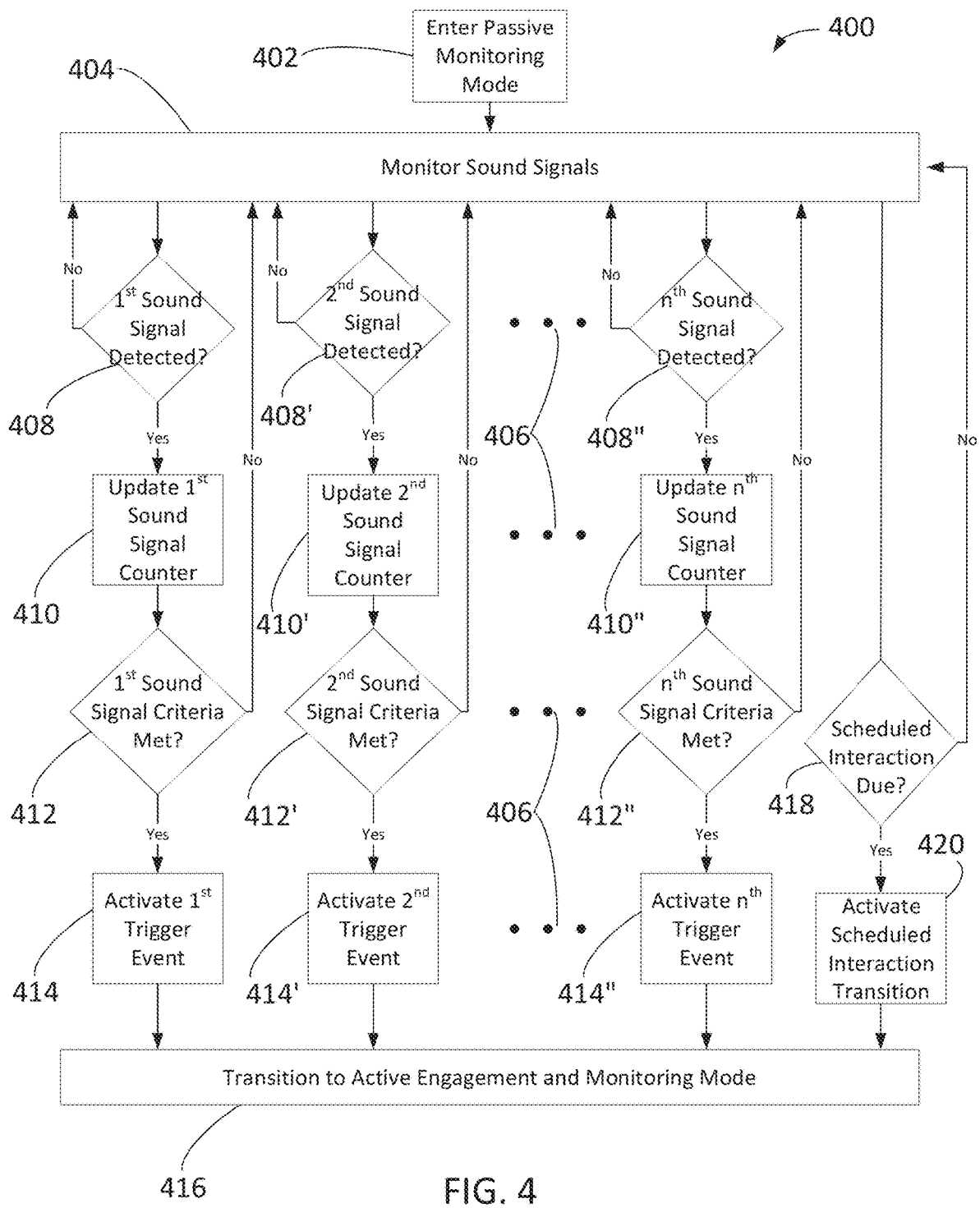
FIG. 4 is a flowchart setting forth steps of an example passive monitoring mode of a virtual health assistant system, in accordance with one or more embodiments of the invention.

Referring now specifically to FIG. 4, a flowchart 400 is illustrated showing the passive monitoring mode of operation. The VHA system 200 can enter the passive monitoring mode 302, at step 402. After entering the passive monitoring mode 302, the VHA system 200 can begin to monitor the sound signals in the environment, at step 404. While monitoring the sound signals, at step 404, the VHA system 200 can be preset to both monitor various sound signals and also check for scheduled interactions.

Some possible sound signals that can be monitored in passive monitoring mode 302 are, for example, coughing, snoring, sneezing, fire alarms, running water, broken glass noises, door knocks, an unknown (and potentially unauthorized) speaker in the acoustic environment, long silences, the user 122 talking to oneself, fatigue indicators, dog barking, loud noises (which may correspond to falls, dropped items, or any other sound signal desired to be monitored). Each sound signal may have a sound signature/pattern/"fingerprint" that can help identify the sound signal (with a certain confidence level). Thus, in addition to providing information for use in general health assessments, passive monitoring of a sound environment of, for example, a house may be used to infer the security and well-being of the home occupants by detecting anomalous or unexpected sound signals that could indicate potential threats and/or high-risk situations like unfamiliar speakers in the house.

Some possible scheduled interactions that the VHA system 200 could check for are, for example, reminders for daily medications, commencement of periodic health questionnaires, memory test or any other possible scheduled interaction with the user 122.

As illustrated, the flowchart 400 illustrates various flow paths for $1^{st}$ through $n^{th}$ sound signals. A $1^{st}$ flow path, a $2^{nd}$ flow path, and an $n^{th}$ flow path are shown for the $1^{st}$, $2^{nd}$, and $n^{th}$ sound signals, and ellipses 406 are included to signify that the VHA system 200 can be configured to monitor for any number of sound signals prescribed by the user 122 following a similar flow path. Additionally, as these flow paths are substantially similar, the following description of the $1^{st}$ flow path also pertains to the $2^{nd}$ through $n^{th}$ flow paths. Further, steps in the $2^{nd}$ flow path will be labeled similarly in the prime series (e.g., step 408 and step 408'), and steps in the $n^{th}$ flow path will be labeled similarly in the double-prime series (e.g., step 408 and 408"). It will be understood that the following flow path description is intended to provide an example, and is in no way intended to be limiting.

While monitoring the sound signals, at step 404, the VHA system 200 can determine, at step 408, whether a $1^{st}$ sound signal has been detected. The $1^{st}$ sound signal can be any of the previously described possible sound signals. Upon determining that the $1^{st}$ sound signal has not been detected, at step 408, the VHA system 200 can return to monitoring the sound signals, at step 404. Upon determining that the $1^{st}$ sound signal has been detected, at step 408, the VHA system 200 can update a $1^{st}$ sound signal counter, at step 410. The $1^{st}$ sound signal counter can be used to keep track of the number of times the $1^{st}$ sound signal is detected and the frequency with which the $1^{st}$ sound signal is detected over a given time period. This information can then be stored in the temporal database 202 and selectively used by the VHA system 200 or a user 122 to adapt or update the rules engine 210, as will be described below.

After updating the $1^{st}$ sound signal counter, at step 410, the VHA system 200 can determine if a $1^{st}$ sound signal criteria has been met, at step 412. The sound signal criteria can indicate, for example, a frequency or other condition or criterion. It should also be noted that the $1^{st}$ sound signal criteria can be set and reset by the rules engine 210 periodically based on user 122 or autonomous adaptation of the rules engine 210, as will be described below.

Upon determining that the $1^{st}$ sound signal criteria has not been met, at step 412, the VHA system 200 can return to monitoring the sound signals, at step 404. Upon determining that the $1^{st}$ sound signal criteria has been met, at step 412, the VHA system 200 can activate a $1^{st}$ trigger event 306, at step 414. Activating the $1^{st}$ trigger event 306, at step 414, transitions the VHA system 200 into the active engagement and monitoring mode, at step 416.

Additionally, while monitoring the sound signals, at step 404, the VHA system 200 can determine whether there is a scheduled interaction due, at step 418. Upon determining that there is not a scheduled interaction due, at step 418, the VHA system 200 can return to monitoring the sound signals, at step 404. Upon determining that there is a scheduled interaction due, at step 418, the VHA system 200 can activate the scheduled interaction transition 307, at step 420. Once the scheduled interaction transition 307 is activated, at step 420, the VHA system 200 transitions into the active engagement and monitoring mode 304.

It should be appreciated that throughout operation in the passive monitoring mode 302, at each step described above, for each of the $1^{st}$ through the $n^{th}$ sound signals, as well as the scheduled interactions, the VHA system 200 can collect data from the analysis module 206 and store that data in the temporal database 202 to be used in an adaptation of the rules engine 210, as will be described in detail below. In certain implementations, in the passive monitoring mode 302, the VHA system 200 may only be monitoring pre-defined sound signals of interest and does not store/save all of the input data 201, thus preserving user privacy. For example, during passive monitoring, the VHA system 200 may be collecting data pertaining to the identification of coughs in a sound stream. In this case, the VHA system 200 may be ignoring other sound signals in the input data 201 that are not medically relevant (e.g., specific words, laughter, etc.).

Generally, the VHA system 200 switches from the passive monitoring mode 302 to the active engagement and monitoring mode 304 to engage in a dialogue with the user 122 in an effort to validate detected sound signals and/or augment detected sound signals with extra information. This validation by the VHA system 200 both confirms that the VHA system 200 should take action, and also helps to self-calibrate or self-train the VHA system 200 through adaptation, as will be described below.

Figure 5:
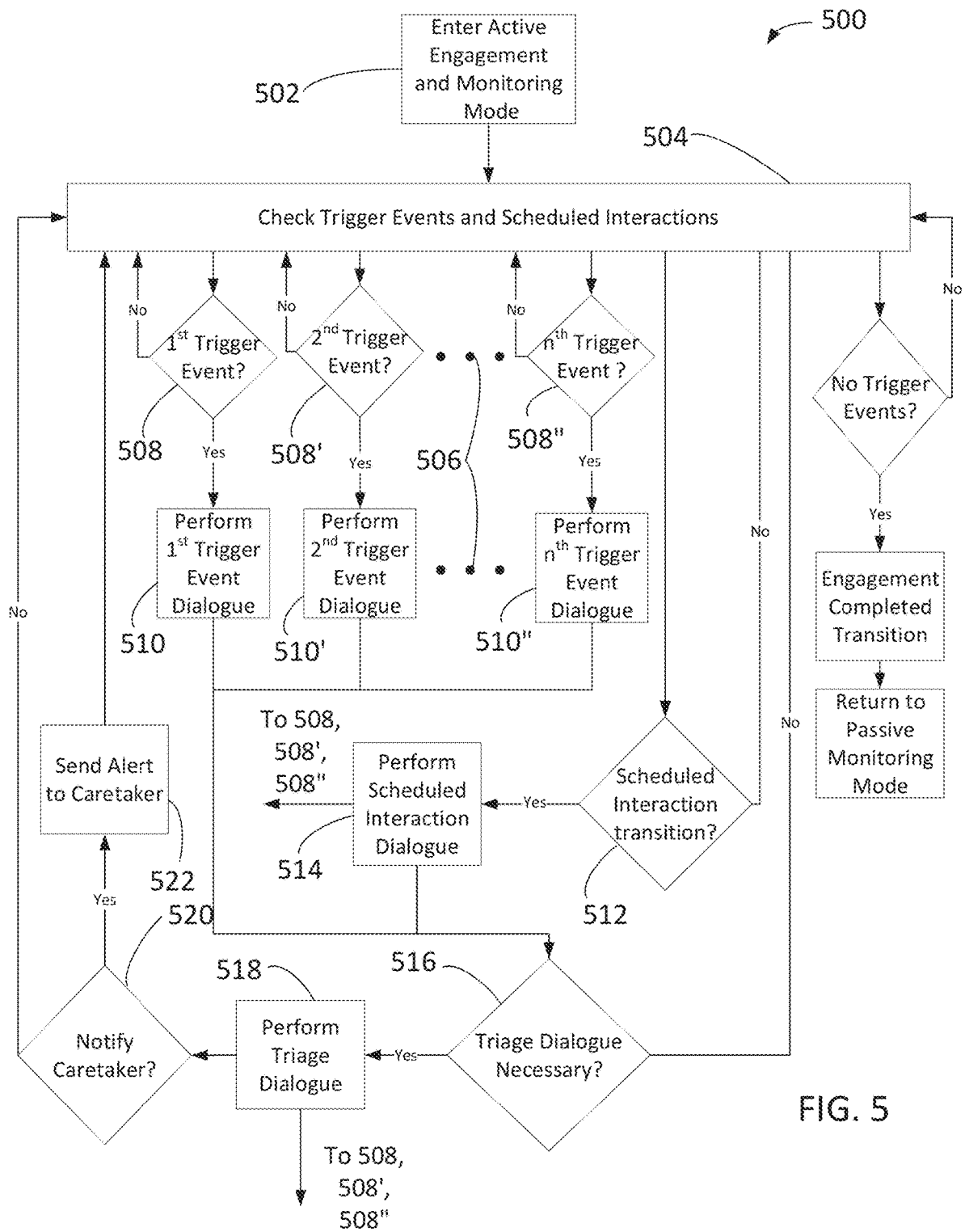
FIG. 5 is a flowchart setting forth steps of an example active engagement and monitoring mode of a virtual health assistant system, in accordance with one or more embodiments of the invention.

Referring now specifically to FIG. 5, a flowchart 500 is illustrated showing the active engagement and monitoring mode of operation. The VHA system 200 can enter the active engagement and monitoring mode 304, at step 502. After entering the active engagement and monitoring mode 304, at step 502, the VHA system 200 can then check the various trigger events and scheduled interactions, at step 504.

As illustrated, similar to the flowchart 400, the flowchart 500 illustrates various flow paths for $1^{st}$ through $n^{th}$ trigger events. A $1^{st}$ flow path, a $2^{nd}$ flow path, and an $n^{th}$ flow paths are shown for the $1^{st}$, $2^{nd}$ and $n^{th}$ trigger events, and ellipses 506 are included to signify that the VHA system 200 can be configured to actively engage the user 122 in response to any number trigger events prescribed by the user 122 following a similar flow path. Additionally, as each of these flow paths are substantially similar, the following description of the $1^{st}$ flow path also pertains to the $2^{nd}$ through $n^{th}$ flow paths. Further, steps in the $2^{nd}$ flow path will be labeled similarly in the prime series (e.g., step 508 and step 508'), and steps in the $n^{th}$ flow path will be labeled similarly in the double-prime series (e.g., step 508 and 508"). It will be understood that the following flow path description is intended to be an example, and is in no way intended to be limiting.

While checking the trigger events at step 504, the VHA system 200 can determine whether the $1^{st}$ trigger event has been activated, at step 508. Upon determining that the $1^{st}$ trigger event has not been activated, at step 508, the VHA system 200 can return to checking the remaining trigger events, at step 504. Upon determining that the $1^{st}$ trigger event has been activated, at step 508, the VHA system 200 can perform a $1^{st}$ trigger event dialogue with the user 122, at step 510. For example, in some instances, the $1^{st}$ trigger event indicates that coughing has been detected and has met or exceeded a threshold coughing criteria. In these instances, the $1^{st}$ trigger event dialogue may be directed at following up to confirm the detected coughing and collect more information from the user 122 relevant to the cough condition. This information can be stored in the temporal database 202 and can be used to adapt the rules engine 210 manually or autonomously, as will be described below.

While checking the trigger events and scheduled interactions, at step 504, the VHA system 200 can determine whether a scheduled interaction transition has been activated, at step 512. Similarly, upon determining that the scheduled interaction transition has not been activated, at step 512, the VHA system 200 can return to checking the remaining trigger events, at step 504. Upon determining that the scheduled interaction transition has been activated, at step 512, the VHA system 200 can perform a scheduled interaction dialogue, at step 514.

In some instances, the scheduled interaction dialogue can pertain to various prescheduled events (that correspond to particular sound signals). For example, the dialogue may comprise a questionnaire for activities of daily living, such as eating habits, or administering a cognitive assessment test. In some other instances, the scheduled interaction dialogue can pertain to a periodic reminder interaction. For example, the dialogue may comprise a daily, weekly, or monthly medication reminder.

After performing any of the various dialogues pertaining to any of the trigger events and/or the schedule interaction transition, the VHA system 200 can determine, at step 516, whether a triage dialogue is necessary. The VHA system 200 determines that the triage dialogue is necessary by interpreting the responses provided by the user 122 (alone or in combination with other acoustic or other data), and making a decision, based on rules provided by the rules engine 210, regarding whether or not the responses warrant sending an alert to a caregiver (or other system). Upon deciding that the triage dialogue is not necessary, at step 516, the VHA system 200 can return to checking the remaining trigger events and scheduled interactions, at step 504.

Upon determining that the triage dialogue is necessary, at step 516, the VHA system 200 can perform the triage dialogue, at step 518. After performing the triage dialogue, at step 518, the VHA system 200 can then determine whether or not it is necessary to notify the caretaker, at step 520. Upon determining that it is necessary to notify the caretaker, at step 520, the VHA system 200 can send an alert to the caretaker, at step 522. Upon determining that it is not necessary to notify the caretaker, at step 520, the VHA system can return to checking the remaining trigger events and scheduled interactions.

For example, in response to the coughing example provided above, during the triage dialogue, at step 518, the VHA system 200 may ask the user 122 a question such as, "Since you've been coughing for several days, and have been running a fever, I'd like to let your doctor know. Is that okay?" In this instance, if the user 122 replies that it is okay for the VHA system 200 to notify the caretaker (or does not reply, which may indicate something is wrong), the VHA system 200 can determine that it is necessary to notify the caretaker, at step 520, and can further send an alert to the caretaker, at step 522. If the user 122 alternatively replies that the caretaker should not be notified, the VHA system 200 can determine that it is not necessary to notify the caretaker, at step 520, and the VHA system 200 can return to checking the remaining trigger events and scheduled interactions. At either step 514 or step 518 (indicated by arrows 524, 526, respectively), during the interaction or triage dialogue, if it is determined by the VHA system 200 that another issue exists, the VHA system 200 may return to the steps 508, 508', 508" to determine if the $1^{st}$, $2^{nd}$ and $n^{th}$ trigger events have been have been activated. In this situation, the VHA system 200 would proceed through the flow paths of FIG. 5 as discussed above.

In some instances, questionnaires administered through the active engagement and monitoring mode can regularly assess a capability of the user 122 to perform activities of daily living (ADLs), nutrition, mobility, and social interaction. The active engagement and monitoring mode can also administer disease severity instruments for cognitive decline, such as the Western Aphasia Battery (WAB) and Mini-Mental State Evaluation (MMSE).

Figure 6:
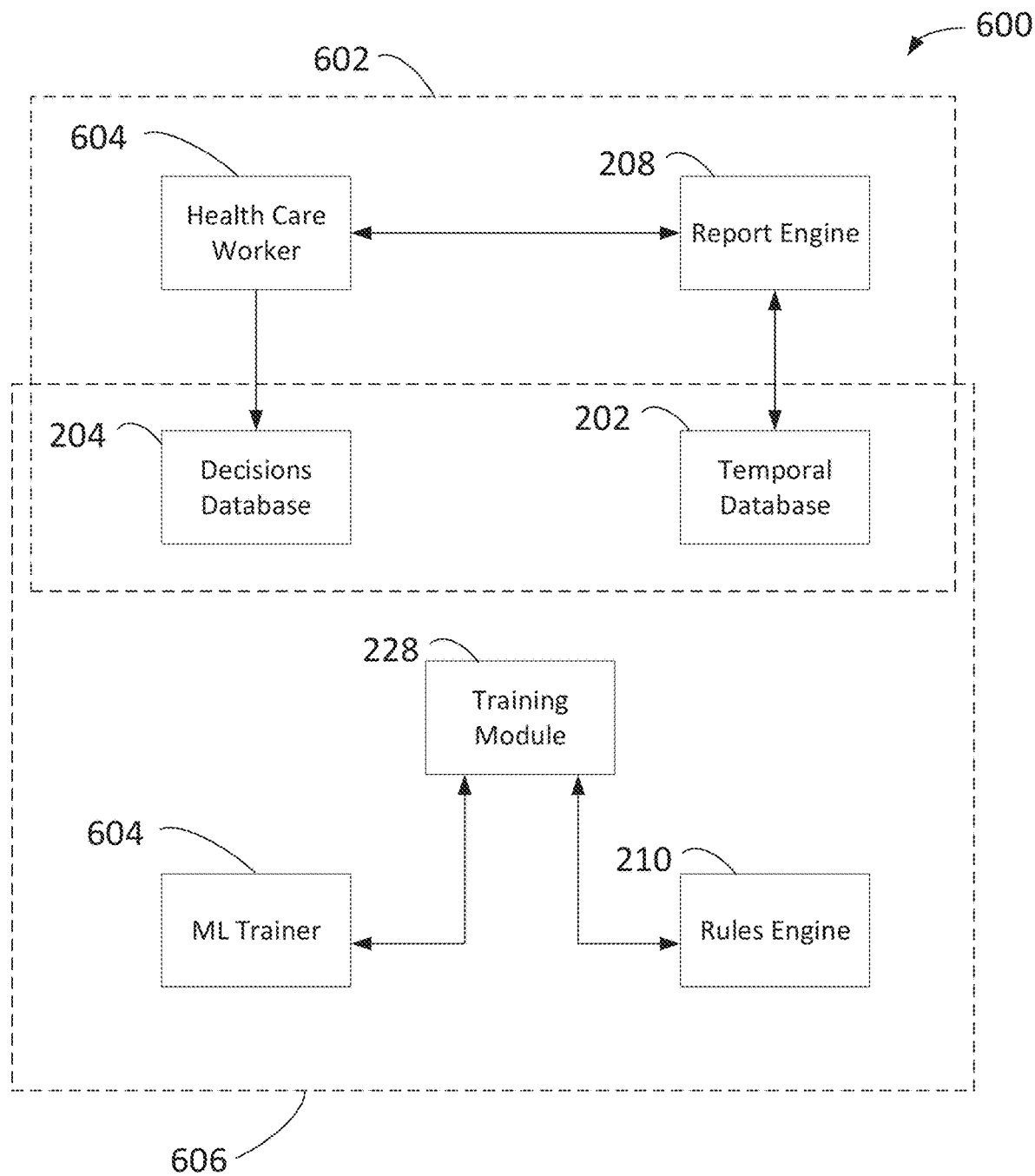
FIG. 6 is a schematic illustrating an example health care query and decision process and an example adaptation process of a virtual health assistant system, in accordance with one or more embodiments of the invention.
Figure 7:
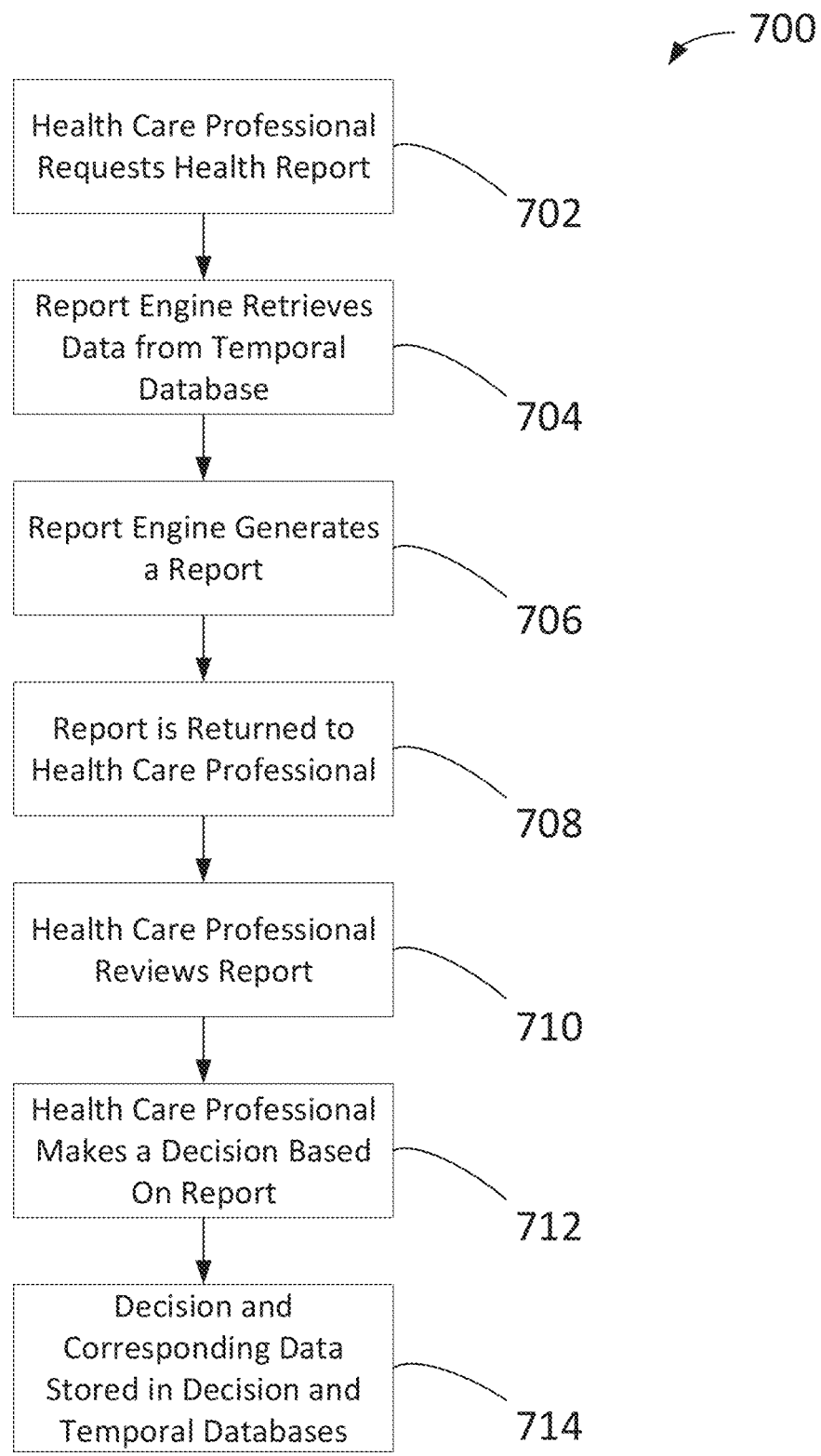
FIG. 7 is a process diagram illustrating example steps of the health care query and decision process of FIG. 6, in accordance with one or more embodiments of the invention.

Referring to FIG. 6, a schematic diagram 600 is provided illustrating various components of the VHA system 200 in relation to an exemplary health care query and decision process 602, initiated by a health care professional 604, and an exemplary adaptation process 606, initiated by a machine learning trainer 608. It will be appreciated that these processes are provided as examples of functionality of the VHA system 200 and are in no way meant to be limiting. Referring to FIG. 7, a process diagram 700 of the health care query and decision process 602 is provided. As illustrated, the health care professional 604 may initiate the process by requesting a health report from the report engine 208, at step 702. The report engine 208 then retrieves data about the user 122 from the temporal database 202, at step 704. The report engine 208 then uses the data to generate a report, at step 706.

The reports are typically requested and generated after at least some active engagement have taken place. The reports are further typically provided in either human-readable form or in data-exchange formats (e.g., JSON, XML, proprietary binary, etc.) and summarize the input data 201 from the user 122 including both the active patient information acquired from responses provided by the user 122 during active engagement and passive patient information acquired during passive monitoring of the user 122. However, although the illustrated process 602 includes a health care professional 604 requesting a health report, reports including passive patient information acquired during passive monitoring can be generated at regular intervals (e.g. twice a day) aggregating the statistics of the sound signals and/or trigger events collected (e.g. type, duration and frequency of cough epochs), and can be delivered as requested.

The VHA system 200 can further determine the type of report to be generated in a variety of methods. For example: (i) the health care professional 604 can specify the type of report to be produced, and can further specify the collected information and statistics to be included in the report, (ii) the user 122 can specify the type of report to be produced, including what information should be presented to others (e.g. family members) or him/herself, (iii) the VHA system 200 can make a decision on what kind of report should be produced based on prior examples, via machine learning algorithms, and internal rules executed by the training module 228 and the rules engine 210, as will be described below. As an example, a report intended for a doctor may be formatted differently and may contain different information than a report intended for the user or for a relative of the user. In the last case the contents of the report could be confirmed by the subject or the caregiver before the report is generated, unless the subject or the caregiver chooses to waive that option.

After the report has been generated, at step 706, the report is returned to the health care professional 604, at step 708. The health care professional 604 then reviews the report, at step 710, and makes a decision based on the report, at step 712. The decision, as well as the corresponding data can then be stored in the decisions database 204 and the temporal database 202, at step 714. Over time, the decisions database 204 and the temporal database 202 can retain records of decisions and corresponding data that led to the health care professional 604 making those decisions. These databases 202, 204 can then be used as bases for updating the rules engine 210 through the adaptation process 606, described below.

Figure 8:
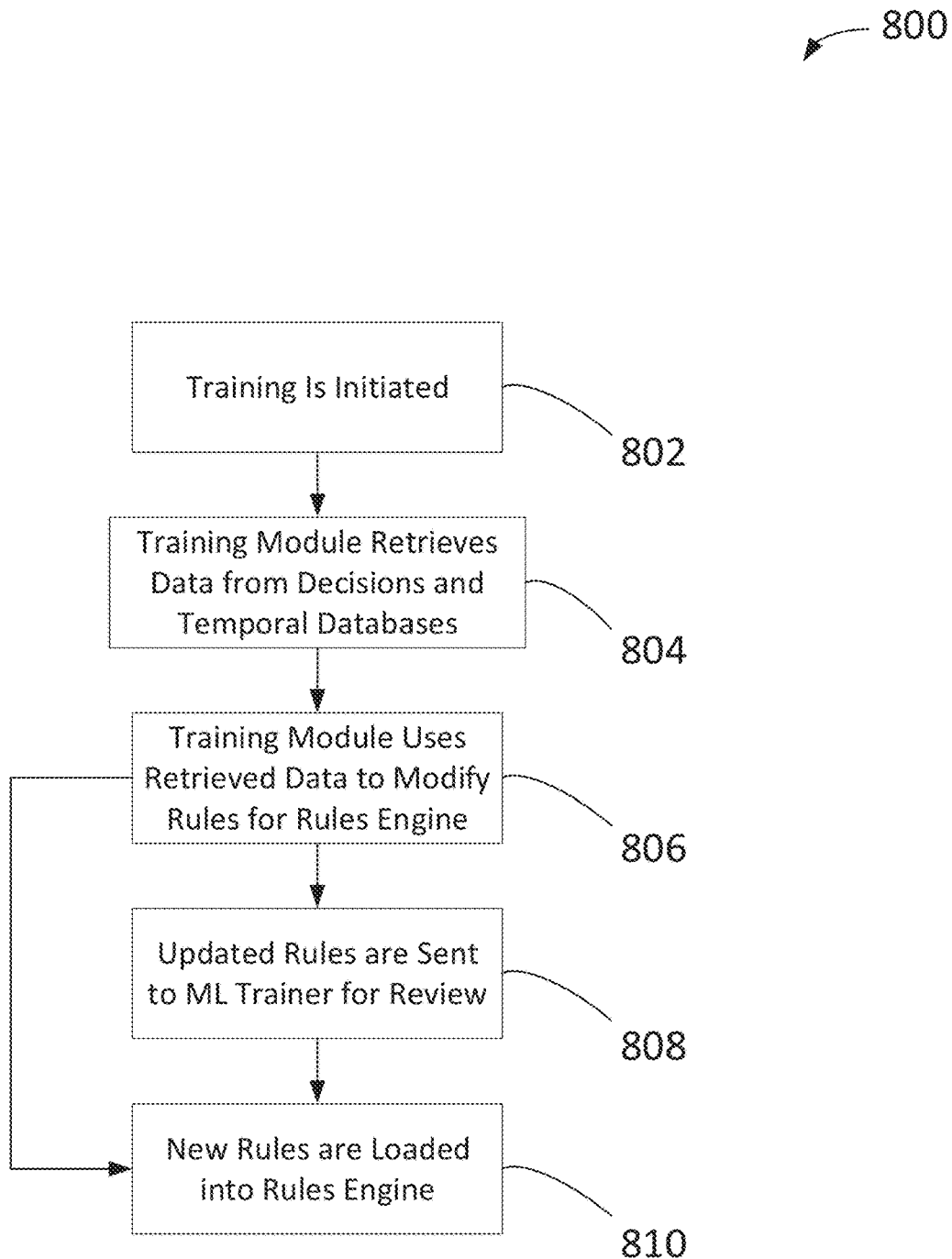
FIG. 8 is a process diagram illustrating the example steps of the adaptation process of FIG. 6, in accordance with one or more embodiments of the invention.

Referring now to FIG. 8 a process diagram 800 of the adaptation process 606 is provided. As illustrated, the machine learning (ML) trainer 608 initiates the process. In some instances, the machine learning trainer 608 can be a technician who initiates the training, at step 802. In other instances, the machine learning trainer 608 is automatically initiated. In some instances, the VHA system 200 may be programmed to initiate training on an automatic and/or periodic basis. For example, in some other instances, the VHA system 200 may be programmed to initiate training automatically based on a periodic schedule (e.g., twice daily, or within a certain time following a sound signal and/or a trigger event) or based on interactions with the user 122, without requiring initialization from a technician. Once the training is initialized, at step 802, the training module 228 retrieves data from both the decisions database 204 and the corresponding patient data from temporal database 202, at step 804. The training module 228 then uses the data retrieved from the decisions database 204 and the temporal database 202 to derive new rules and revise or eliminate existing rules. Thus, in some instances, the training module 228 devises the new rules and/or revises or eliminates existing rules based on passive and active patient data obtained by the VHA system 200 and corresponding decisions made by the health care professional 604. In some instances, when the adaptation process 606 was initiated by the ML trainer 608, the training module 228 may then send the modified rules to the ML trainer 608 for review, at step 808. After the modified rules have been reviewed, they can then be loaded into the rules engine 210, at step 810. In the cases where the adaptation process 606 was not initiated by the ML trainer, 608, the modified rules can be loaded into the rules engine 210 without review, in which flow would proceed directly from step 806 to step 810, as indicated in FIG. 8.

In some other instances, the adaptation process 606 described above may be used to adapt the active engagement and monitoring mode 304 as it collects the input data 201 from the user 122 based on prior responses from the user 122 retrieved from the temporal database 202. For example, an active engagement about coughing may also typically request information about allergies. However, if the system collected that information earlier, while engaging in an interaction about sneezing, the rules engine 210 will have received modified rules through the adaptation process 606, thereby adapting the dialogue regarding coughing, as there is no reason to repeat that portion of the dialogue again. Another example of the adaptation process 606, may include adapting the style of the interaction. For example, if fatigue is detected in a recent interaction, then the rules engine 210 will have received modified rules aimed at reducing questions when another trigger event is detected and attempting to encourage the user 122 to rest.

In yet other instances, the VHA system 200 can go through the adaptation process 606 whenever a trigger event forces the VHA system 200 into the active engagement and monitoring mode 304. In these instances, the adaptation process 606 can cause the VHA system 200 to adapt its responses and actions based on continuously analyzed detected signals and interactions with the user 122. For example, if a "too much coughing" rule is triggered, the VHA system 200 may inquire about the trigger by asking, for example, "It seems that you have been coughing a lot. May I ask a few questions?" If the user 122 responds, "Ask me in an hour," then the VHA system 200 adapts by waiting an hour and then switching back into active engagement with the user 122. Likewise, if the VHA system 200 asks several questions based on coughing and learns that the user 122 has extensive chest pain, it could then switch to questions or tests related to a possible heart attack. That is, the VHA system 200 adapts its queries and responses to input data 201 from the user 122.

In other instances, the VHA system 200 can use the adaptation process 606 to modify sensitivity of the VHA system 200 during both passive monitoring mode 302 and active engagement and monitoring mode 304 to, for example, shift toward more falsely detected trigger events pertaining to critical conditions.

In some other instances, the VHA system 200 can use the adaptation 606 to not only monitor sounds signals and detect trigger events, such as, for example, a cough or a cough epoch, but also adaptively learn to distinguish between detected sound signals of the same type based on characteristics of the input sound signal. The adaptation process 606 can also be used to determine which sound signals are monitored during passive monitoring mode 302. For example, if fatigue was detected during an interaction with the user 122 during the day, the passive monitoring mode 302 may be adapted to monitor for various indications of poor sleep quality, such as, for example, snoring, sleep apnea, or any other suitable sleep characteristics.

Referring now to FIG. 9, another VHA system 900 is provided in accordance with the present invention. The VHA system 900 includes a VHA remote storage and processing facility or a VHA cloud 902 (which may be referred to as a remote device). The VHA cloud 902 is a "cloud-based" computing resource that can store data, process incoming information, generate reports, and host rule-modification software (e.g., on remote servers). The VHA cloud 902 allows for one or more home-based VHA modules 904, mobile VHA modules 906, and health care VHA modules 908 (which may be referred to as local electronic devices). Each of the various VHA modules 904, 906, 908 can be generally similar to and/or have all or some of the components of the VHA system 200 described above, while being tailored for differing settings. The home-based VHA modules 904 are disposed in homes of various users. The home-based VHA modules 904 monitor environments, monitor sound signals, detect trigger events, and interact with the users, as described above, with reference to the VHA system 200. There can be one or more sets of the home-based VHA modules 904 in any one home and many different homes containing the home-based VHA modules 904 can interact with the VHA cloud 902. It is noted that the system can learn not only from its interactions with a particular user, but from those of other users elsewhere. For example, if the system learns that a certain sound signature is associated with a certain object falling on a certain type of floor, or with a user falling in a certain way, that pattern can be shared for use with monitoring of other users. Also, with the permission of the user, a voice of a suspected intruder in a user's home can be compared with a voice (if available) of a person being sought by the law enforcement (or otherwise of a person unauthorized due to, e.g., a restraining order) when, for example, it is believed that the person being sought is near the user's home (and if voices match, law enforcement may be automatically notified).

As such, the decisions databases and temporal databases of the various modules 904, 906, 908 can be manually or automatically uploaded or sent to the VHA cloud 902 to form a universal decisions database and universal temporal databases. Each of the various modules 904, 906, 908 can then selectively retrieve information from the universal decisions database and the universal temporal database. Therefore, when new information is gathered by any VHA module 904, 906, 908, the VHA cloud 902 and/or an individual VHA module 904, 906, 908 can draw upon additional information gathered by other modules 904, 906, 908 to aid in analysis and decision making.

Additionally, each of the various modules 904, 906, 908 may be governed by a common universal rules engine, which can be stored and adapted within the VHA cloud 902. The universal rules engine can be adapted through machine learning, as described above, using the adaptation process 606, but has access to significantly more information. That is, the universal rules engine can be adapted through machine learning using information gathered from multiple modules 904, 906, 908 monitoring different users in varying settings. This vast amount of additional information thereby provides a more robust or larger data set for the VHA system 900 to learn from.

In some illustrative embodiments, a universal decisions database, a universal analysis module (including one or more of its sub-modules), a universal report engine, and a universal temporal database (see elements 202, 204, 206, and 208) may be stored and adapted within the VHA cloud 902. In such an embodiment, each of the various modules 904, 906, 908 may have basic functionality thereon to communicate with the VHA cloud 902 and the VHA cloud may analyze data from the respective modules 904, 906, 908 and make decisions based on the analyzed data, wherein the decisions are communicated to the respective modules 904, 906, 908 for implementation.

The mobile VHA modules 906 also monitor sound signals, detect trigger events, and interact with various users, as described above, with reference to the VHA system 200, but may be programmed to operate using a mobile device, such as, for example, a smartphone, a tablet, or any other suitable device (which may provide processing capabilities and inputs such as one or more microphones or cameras).

The health care VHA modules 908 are used mainly by health care professionals and family members and provide interfaces to the VHA cloud 902. Through the VHA cloud 902, this allows health care professionals and family members to interface with appropriate home-based and mobile VHA modules 904, 906. The health care VHA modules 908 retrieve data and reports from the cloud, generate alerts, allow approved personnel to modify rules, and interface to other health care IT systems (e.g., electronic medical-record systems).

Figure 10:
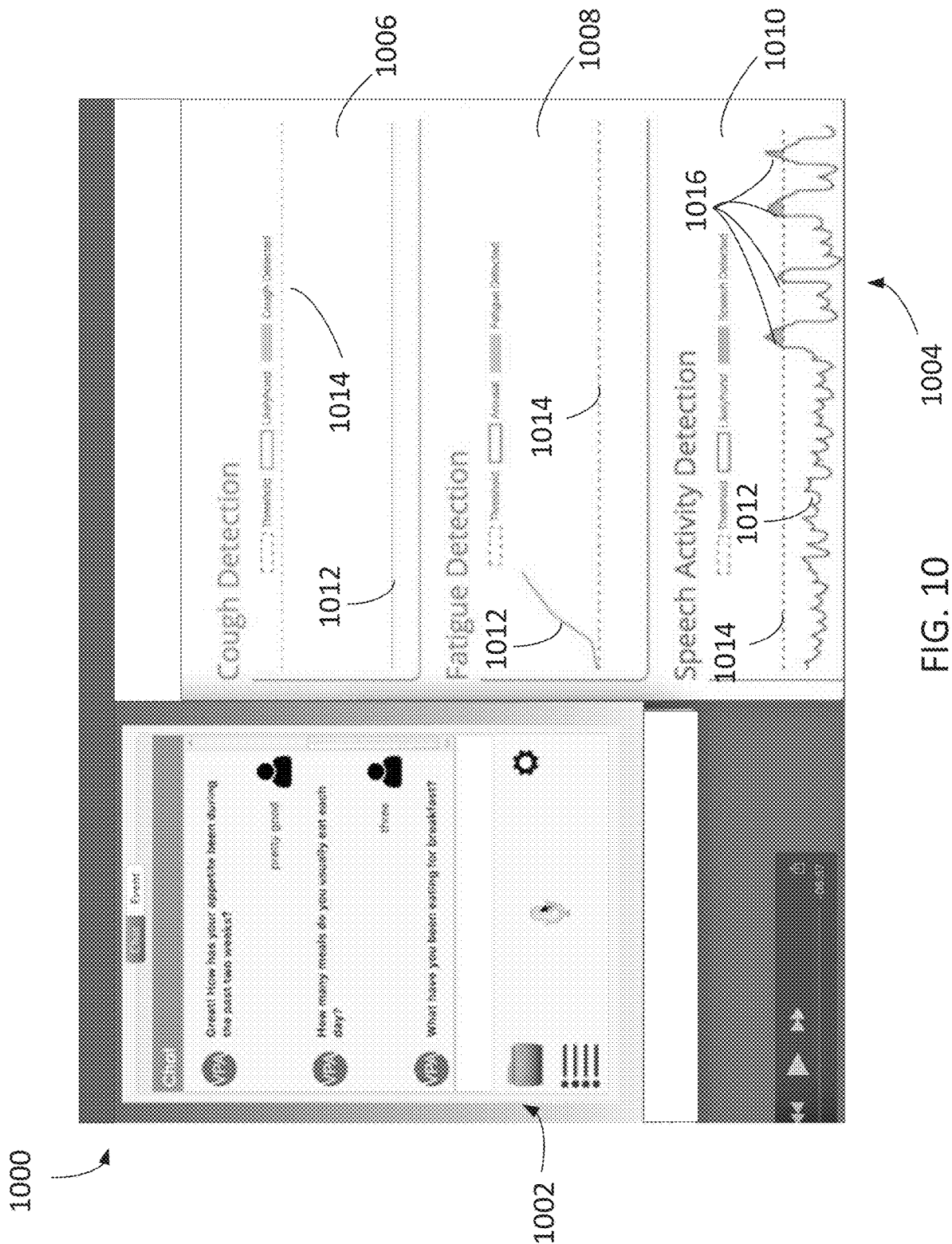
FIG. 10 is a schematic illustrating an example user interface of a virtual health assistant system, in accordance with one or more embodiments of the invention.
Figure 11:
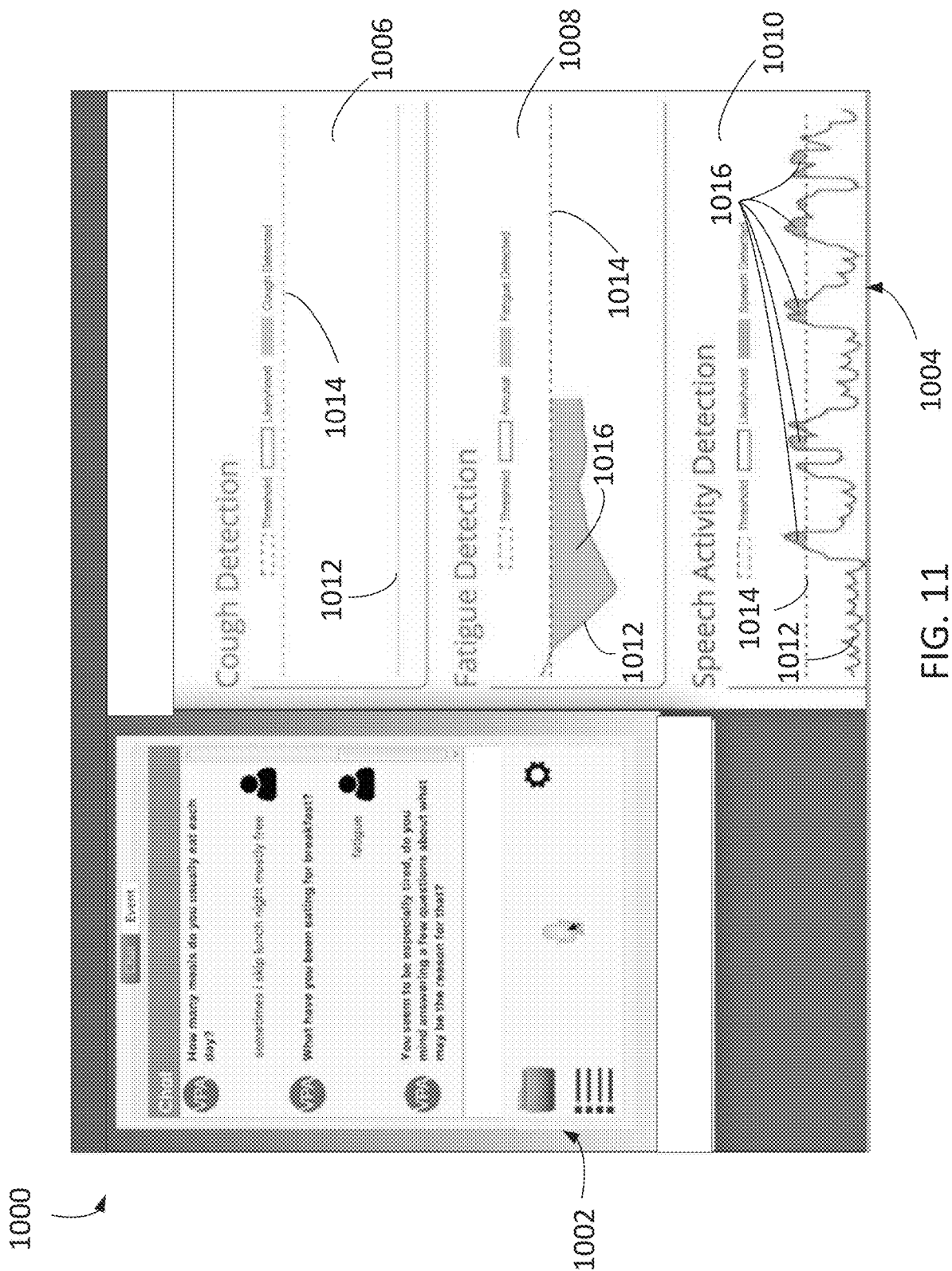
FIG. 11 is a schematic illustrating the example user interface of FIG. 10, showing continued dialogue, in accordance with one or more embodiments of the invention.
Figure 12:
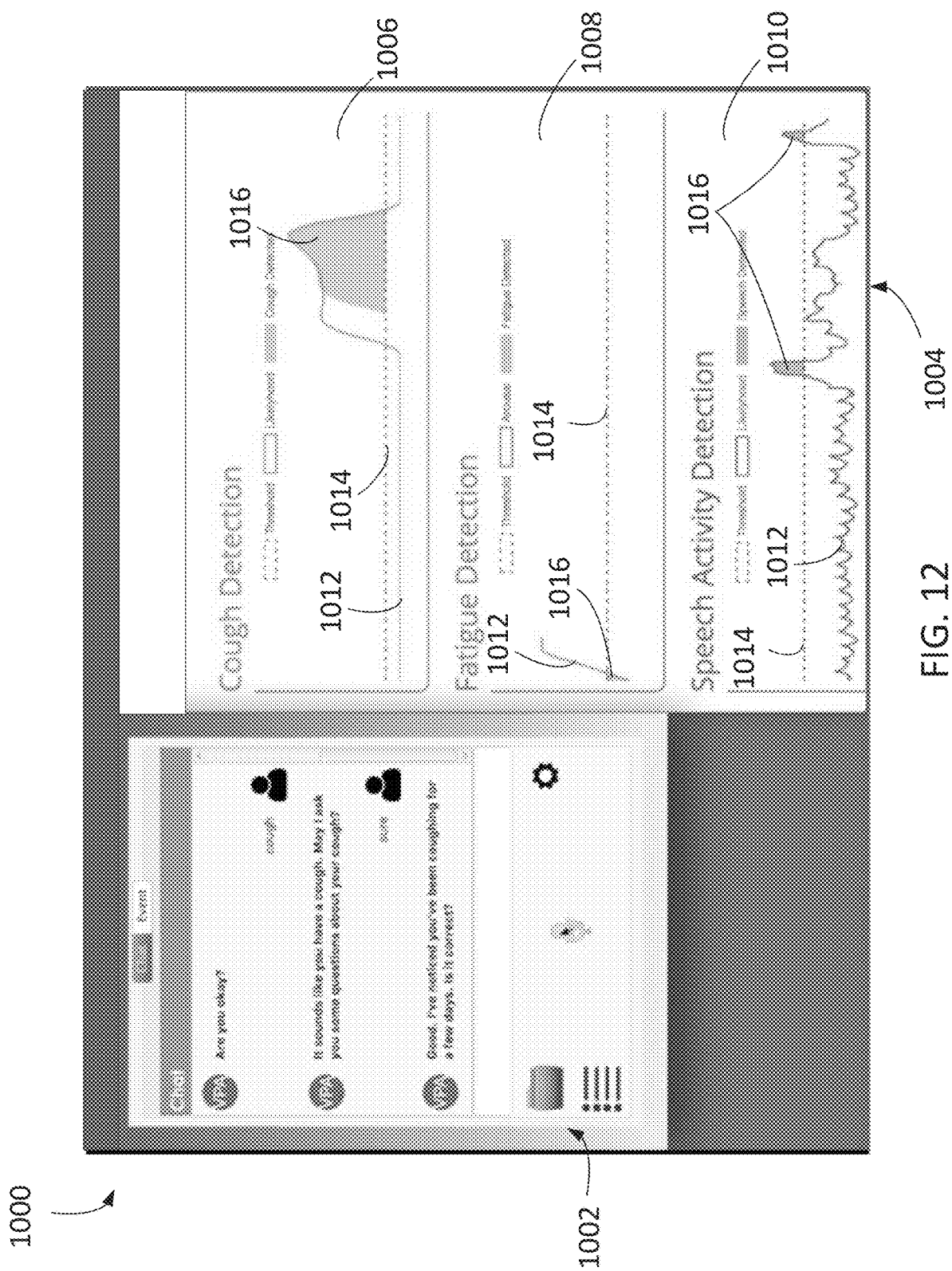
FIG. 12 is a schematic illustrating an example user interface of a virtual health assistant system, in accordance with one or more embodiments of the invention.

Referring now to FIGS. 10-12, an exemplary user interface 1000 is provided in accordance with the present invention. The exemplary user interface 1000 is configured for use with any of the VHA systems 100, 200, 900 and/or any of the VHA modules 904, 906, 908 described above. The user interface 1000 includes a conversation pane 1002 and a monitoring pane 1004. The conversation pane 1002 displays a dialogue between the VHA system 100, 200, 900 or the VHA module 904, 906, 908 and the user 122. The monitoring pane 1004 includes a first detection chart 1006, a second detection chart 1008, and a third detection chart 1010. Each of the three detection charts tracks a continuously-monitored sound signal detection value 1012, corresponding to a level of detection of a given sound signal. Exemplary sounds signals shown being monitored by the VHA system 100, 200, 900 or VHA module 904, 906, 908 are cough, fatigue, and speech activity. It should be noted that, although the exemplary monitoring pane 1004 includes three detection charts 1006, 1008, 1010, in some other aspects, the monitoring pane 1004 can include fewer or more than three detection charts. Furthermore, the number of detection charts displayed on the user interface 1000, as well as the specific sounds signals being monitored, may be chosen by the user 122. The monitored sound signals can further include any of the various sound signals described above, including, but not limited to, coughing, snoring, sneezing, fire alarms, broken glass noises, door knocks, an unknown (and potentially unauthorized) speaker in the environment, long silences, the user 122 talking to oneself, fatigue indicators, loud noises, or any other pertinent sound signal chosen by the user 122 to be monitored.

Each of the continuously-monitored sound signal detection values 1012 is further tracked against a corresponding sound signal detection threshold value 1014, corresponding to a threshold detection value for the given sound signal. The sound signal detection threshold value 1014 may be an upper limit, for example, when monitoring coughing of the user 122, the sound signal detection threshold value 1014 may be, for example, five coughs detected within ten minutes. In this instance, if the VHA system 100, 200, 900 or VHA module 904, 906, 908 detects five or more coughs within ten minutes, it triggers a trigger event. Alternatively, the threshold value 1014 may be a lower limit, for example, when monitoring fatigue of the user 122, the sound signal detection threshold value 1014 may be a detected amount of sound energy output from the user 122. In this instances, when the VHA system 100, 200, 900 or VHA module 904, 906, 908 detects an amount of sound energy output lower than the sound signal detection threshold value 1014, it triggers a trigger event. The sound signal detection threshold value 1014 can be selected manually, through input from the user 122, or autonomously, based on machine learning, using the adaptation process 606, as described above.

The monitoring pane 1004 further indicates sound signal occurrences 1016. These sound signal occurrences 1016 indicate that the continuously-monitored sound signal detection value 1012 has met or exceeded (or, in the lower limit instances, dropped below) the sound signal detection threshold value 1014, and that a trigger event has been triggered.

FIG. 10 includes sound signal occurrences 1016 in the third detection chart 1010, corresponding to the detection of speech activity. As illustrated, neither of the first and second detection charts 1006, 1008 include sound signal occurrences. FIG. 11 includes sound signal occurrences 1016 in both the second and third detection charts 1008, 1010, corresponding to both the detection of speech activity and the detection of user fatigue. As illustrated, the first detection chart 1006 does not include any sound signal occurrences. FIG. 12 includes sound signal occurrences 1016 in the first, second, and third detection charts 1006, 1008, 1010, corresponding to the detection of coughing, the detection of fatigue, and the detection of speech activity. As such, the VHA system 100, 200, 900 or the VHA module 904, 906, 908 can be used to monitor multiple different sound signals.

It should be noted that any of the VHA systems 100, 200, 900, any of the VHA modules 904, 906, 908, any of their corresponding features, or any other various features, such as the user interface 1000, disclosed herein can be used in various combination with each other, as desired for a given situation. These combinations have been considered and are well within the scope of the present disclosure.

As such, the present invention provides VHA systems that ensure safety of the user by continuous passive monitoring for anomalous sound signals (falls, fire alarm or broken glass noises) and unfamiliar speakers at home. If a concerning sound signal is detected, the system would engage VPA (active engagement and monitoring mode), to verify with user and reduce reported false alarms. The system would verify if there is an action to take (like call the emergency services), summarize the necessary information and produce a report to present to care-givers, health care professionals, emergency assistants, or other persons. For example, if a fall is detected and verified (as shown in FIG. 1) the system may follow up with "I'm going to call 9-1-1", to get immediate help. Using speaker verification the system would also ensure that the registered speaker is responding, and engage VPA to verify that detected unregistered speakers are welcome.

The VHA systems disclosed further enable frequent, easily administered, reliable and cost effective wellness screenings.

The VHA systems can additionally monitor for indicators of illness or decline in health over time, and interact with caregivers, so that a health care professional can follow up promptly. A VPA interaction can collect information that can be reported in follow up calls, as needed, with advising nurses, physicians, or other healthcare providers. In aggregate, summarized semantic (e.g., the "digest" of a symptom evaluation) and acoustic data can be made available to health care givers through SMS or email alerts and an intuitive graphical user interface to ensure that telephone follow-up, home care visits, office evaluations, or, if necessary, emergency evacuation to an ER, take place in an efficient, timely and appropriate fashion based on available data.

The VHA systems can further provide assistance and reminders for everyday activities. The VPA systems can serve as a medication reminder, and source of simple solutions for common problems that may affect activities of daily living, risks in the home, or nutritional status. Such an assistant would complement the more thorough assistance from care-givers and clinicians.

The VHA systems can additionally provide high-accuracy automated speech recognition. From an anatomical point of view, studies have shown age-related degeneration with atrophy of vocal cords, calcification of laryngeal cartilage, and changes in muscles of the larynx. Such changes, result in specific features of elderly voices, such as imprecise production of consonants, tremors and slower articulation, making ASR systems trained on regular adult population not very accurate on elderly speakers. The VHA systems can address this problem by applying a high accuracy ASR system for the elderly through robust features and modeling informed by existing data collected from the elderly population.

The present invention has been described in terms of one or more preferred embodiments, and it should be appreciated that many equivalents, alternatives, variations, additions, and modifications, aside from those expressly stated, and apart from combining the different features of the foregoing embodiments in varying ways, can be made and are within the scope of the invention. In the above description, a number of specific details, examples, and scenarios are set forth in order to provide a better understanding of the present disclosure. These examples and scenarios are provided for illustration, and are not intended to limit the disclosure in any way. Those of ordinary skill in the art, with the included descriptions, should be able to implement appropriate functionality without undue experimentation. References in the specification to an "embodiment," an "example," a "version," an "implementation," a "configuration," an "instance," etc., indicate that the embodiment, example, version, etc. described may include a particular feature, structure, or characteristic, but every embodiment, example, version, etc. may not necessarily include the particular feature, structure, or characteristic. Such phrases are not necessarily referring to the same embodiment. Further, when a particular feature, structure, or characteristic is described in connection with an embodiment, it is believed to be within the knowledge of one skilled in the art to effect such feature, structure, or characteristic in connection with other embodiments whether or not explicitly indicated.

The computerized functionality described above may be implemented in hardware, firmware, software, single integrated devices, multiple devices in wired or wireless communication, or any combination thereof. Computerized functions may be implemented as instructions stored using one or more machine-readable media, which may be read and executed by one or more processors. A machine-readable medium may include any mechanism for storing or transmitting information in a form readable by a machine. For example, a machine-readable medium may include any suitable form of volatile or non-volatile memory. In the drawings, specific arrangements or orderings of schematic elements may be shown for ease of description. However, the specific ordering or arrangement of such elements is not meant to imply that a particular order or sequence of processing, or separation of processes, is required in all embodiments. Further, some connections or relationships between elements may be simplified or not shown in the drawings so as not to obscure the disclosure. This disclosure is to be considered as exemplary and not restrictive in character, and all changes and modifications that come within the spirit of the disclosure are desired to be protected.

The invention claimed is:

1. A system for providing health information or assistance, the system comprising:
at least one electronic device configured to engage in verbal communication with at least one user based upon at least one type of signal selected from the group consisting of 1) sound signals from the at least one user's environment, 2) non-verbal signals from the at least one user, 3) verbal signals from the user; and 4) any combination of (1), (2), and (3), the electronic device comprising:
an input module configured to receive the sound signals from the at least one user's environment, the non-verbal signals from the at least one user, and the verbal signals for the at least one user;
a communication module configured to send information related to the at least one user and the at least one user's environment, including the sound signals, the non-verbal signals, and the verbal signals, to a remote device, and to subsequently receive condition signals from the remote device;
a processing module configured to receive the condition signals and to cause the electronic device to operate in a passive monitoring mode or an active engagement and monitoring mode, the active engagement and monitoring mode including, but not limited to, verbal communication with the at least one user;
an output configured to engage the at least one user in specific types of verbal communication selected from a group consisting of: 1) asking the at least one user a question; 2) providing related suggestions to the user; and 3) provide information to the user; and
the remote device comprising:
a remote communication module configured to receive the information related to the sound signals, the non-verbal signals, and the verbal signals from the at least one electronic device, and to subsequently send the condition signals to the at least one electronic device; and
a rules module configured to determine, based on the sound signals, the non-verbal signals, and the verbal signals, a responsive action;
wherein the responsive action is communicated from the remote device to the at least one electronic device in the form of the condition signals.

2. The system of claim 1, wherein at least one of the electronic device and the remote device further comprises:
a speaker identification module configured to identify and authenticate the at least one user.

3. The system of claim 1, wherein the remote device further comprises:
a temporal database configured to receive and store the information related to the at least one user and the at least one user's environment; and
a decisions database configured to receive and store decisions from at least one health care provider.

4. The system of claim 3, wherein the remote device further comprises:
a training module configured to selectively retrieve the information related to the at least one user and the at least one user's environment from the temporal database, selectively retrieve the decisions from the at least one health care provider from the decisions database, and adapt the rules module using machine learning based on the retrieved information and decisions to increase accuracy of the responsive action.

5. The system of claim 4, wherein the at least one electronic device comprises a plurality of electronic devices, the at least one user comprises a plurality of users using the plurality of electronic devices, and wherein the training module is further configured to selectively retrieve information about each of the plurality of users and each of a plurality of users' environments, selectively retrieve decisions from at least one health care provider, and adapt the rules module using machine learning based on the retrieved information and decisions to increase accuracy of the responsive action.

6. The system of claim 3, wherein the communication module of the at least one electronic device is further configured to retrieve the information related to the at least one user, the at least one user's environment, and the decisions from the at least one health care provider, and the at least one electronic device further comprises:
a report module configured to produce a report to the at least one user regarding the information related to the at least one user, the at least one user's environment, and the decisions from the at least one health care provider.

7. The system of claim 1, wherein, when operating in the passive monitoring mode, a remote device processing module is configured to:
analyze the sound signals to extract passive user information;
determine, from the passive user information, whether an active trigger event has occurred; and
upon determining that the active trigger event has occurred, cause the electronic device to transition to the active engagement and monitoring mode.

8. The system of claim 7, wherein, upon transitioning to the active engagement and monitoring mode:
the processing module is configured to engage the at least one user via the verbal communication through the output; and
the remote device processing module is configured to verify and augment the passive user information through the verbal communication with the user.

9. The system of claim 8, wherein, upon transitioning to the active engagement and monitoring mode, the remote device processing module is further configured to:
analyze a sound signal from an input to extract active user information associated with a communication with the at least one user; and
determine, from both the passive user information and the active user information, an active engagement response.

10. The system of claim 9, wherein, upon transitioning to the active engagement and monitoring mode, the remote device processing module is further configured to:
determine, via the verbal communication, whether the active engagement response has been completed; and
upon determining that the active engagement response has been completed, cause the electronic device to transition to the passive monitoring mode.

11. The system of claim 9, wherein the rules module adapts the verbal communication through the output in real time based on one of the passive user information and the active user information.

12. The system of claim 11, wherein an adaptation of the verbal communication comprises changes in questions asked or a way questions are asked to the at least one user based on changes in a condition of the at least one user detected in one of the passive user information and the active user information.

13. The system of claim 1, wherein the non-verbal signals are selected from the group consisting of: pitch, speed, tone, volume of voice, intonation, inflection, or other sounds that do not include words.

14. The system of claim 7 or 9, wherein the step of analyzing the sound signals comprises at least one of analyzing speech pattern, intonation, data about the at least one user, data about the at least one user's environment, sound signals in the at least one user's environment, sounds created by the at least one user, and does not include analyzing key words.

15. The system of claim 9, wherein, while engaging the at least one user via the verbal communication regarding the active trigger event, the rules module adapts future engagements regarding related trigger events based on information acquired during the verbal communication regarding the active trigger event.

16. The system of claim 9, wherein, while engaging the at least one user via the verbal communication, the processing module is configured to analyze both verbal signals and non-verbal signals.

17. The system of claim 5, wherein each of the plurality of electronic devices is configured to produce a report and, subsequent to the training module adapting the rules module, the at least one health care provider makes a decision based on the report.

18. The system of claim 5, wherein machine learning performed by the training module uses a model based on information retrieved from the temporal database and decisions retrieved from the decisions database, and the model is subsequently trained based on input from the at least one health care provider.

19. The system of claim 18, wherein the model is based on information from multiple users, thereby providing a larger data set.

20. The system of claim 5, wherein each of the plurality of electronic devices is configured to produce a report and each of the plurality of users inputs information into a corresponding one of the plurality of electronic devices and receives output information from the corresponding one of the plurality of electronic devices.

* * * * *